(12) United States Patent
Wu et al.

(10) Patent No.: US 8,999,680 B2
(45) Date of Patent: Apr. 7, 2015

(54) PREPARATION OF 1,4-DIAMINOBUTANE

(75) Inventors: Liang Wu, Delft (NL); Petronella Catharina Raemakers-Franken, Budel (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/386,169

(22) PCT Filed: Jul. 20, 2010

(86) PCT No.: PCT/EP2010/060480
§ 371 (c)(1),
(2), (4) Date: Apr. 13, 2012

(87) PCT Pub. No.: WO2011/009859
PCT Pub. Date: Jan. 27, 2011

(65) Prior Publication Data
US 2012/0190087 A1 Jul. 26, 2012

(30) Foreign Application Priority Data
Jul. 24, 2009 (EP) .................................... 09166374

(51) Int. Cl.
*C12P 13/00* (2006.01)
(52) U.S. Cl.
CPC .................................... *C12P 13/001* (2013.01)
(58) Field of Classification Search
None
See application file for complete search history.

(56) References Cited

FOREIGN PATENT DOCUMENTS

| EP | 1 260 588 | 11/2002 |
| JP | 56-151494 | 11/1981 |
| JP | 4-349890 | 12/1992 |
| WO | WO 2006/005603 | * 1/2006 |
| WO | WO 2006/005604 | 1/2006 |

OTHER PUBLICATIONS

International Search Report for PCT/EP2010/060480, mailed Oct. 4, 2010.

* cited by examiner

*Primary Examiner* — Nashaat Nashed
(74) *Attorney, Agent, or Firm* — Nixon & Vanderhye P.C.

(57) ABSTRACT

The present invention relates to a novel method for the preparation of 1,4-diaminobutane [DAB]. The method according to the present invention involves at least one biocatalytic step which comprises the biocatalytic production of at least one N-protected precursor of DAB. The present invention also relates to a method for the preparation of DAB involving at least one biocatalytic step, and comprising the steps of a) biocatalytically preparing an N-protected precursor of DAB yielding a—biocatalytic reaction mixture containing the N-protected precursor of DAB, b) recovering the N-protected precursor from the biocatalytic reaction mixture and c) converting the N-protected precursor into DAB. More in particular, the present invention relates to a method for the preparation of DAB, wherein the at least N-protected precursor of DAB is selected from the group consisting of N5-protected ornithine, N-protected DAB, and N-protected 4-aminobutyraldehyde.

7 Claims, 1 Drawing Sheet

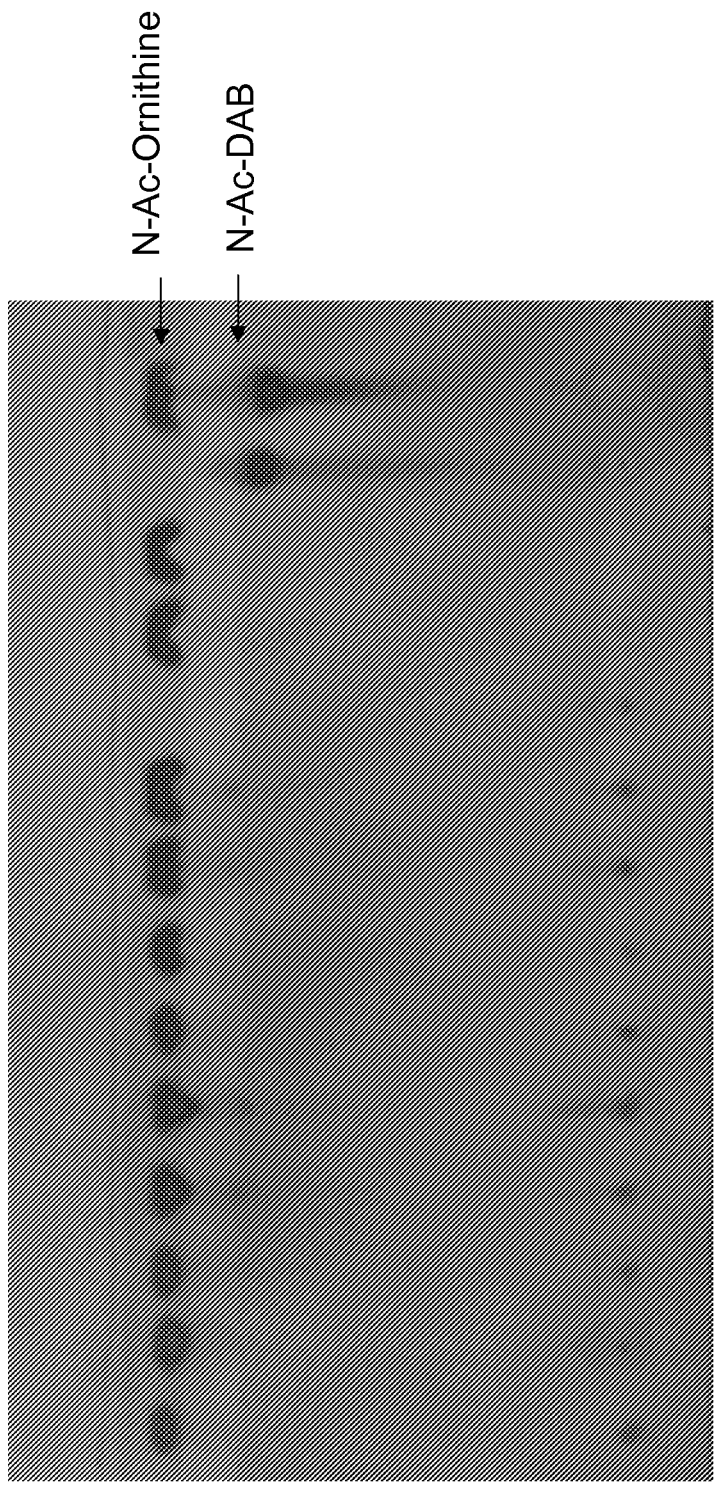

PREPARATION OF 1,4-DIAMINOBUTANE

This application is the U.S. national phase of International Application No. PCT/EP2010/060480, filed 20 Jul. 2010, which designated the U.S. and claims priority to EP Application No. 09166374.0, filed 24 Jul. 2009, the entire contents of each of which are hereby incorporated by reference.

The present invention relates to a method for the preparation of 1,4-diaminobutane [DAB] involving at least one biocatalytic step.

The compound DAB is an important raw material for the production of some of the major engineering plastics: polyamide-4,6, either in the form of a homopolymer, or copolymerized, for example, with about 5 wt. % of polyamide-6 monomer (caprolactam). The homopolymer polyamide-4,6 (nylon-4,6) was described as early as 1938 (U.S. Pat. No. 2,130,948, Carothers). It is the polycondensation product of the monomers DAB and adipic acid. Presently, especially compounds of polyamide-4,6 are being produced and sold by DSM in the Netherlands under the trade name STANYL®.

For the synthesis of DAB a number of chemical routes are known. These chemical routes suffer from the disadvantage that starting materials have to be obtained form sources that are considered to be non-renewable. There exists, however, a substantial need for providing new and feasible routes for the synthesis of DAB starting from renewable carbon sources and using biochemical processes (also referred to as "biotransformation").

A method for the preparation of DAB involving at least one fermentative step has been described in PCT applications published as WO2006/005603 and WO2006/00504. Both documents describe the fermentative production of DAB in a micro-organism having an increased level of an ornithine decarboxylase activity.

The present method relates to an alternative method for the preparation of DAB. The method according to the present invention involves at least one biocatalytic step which comprises the biocatalytic production of at least one N-protected precursor of DAB and subsequent in vitro conversion of the N-protected precursor into DAB.

It has been found that the recovery of DAB after biocatalytic production meets with considerable difficulties. In WO2007/079944 the recovery of an organic amine, such as DAB has been described. In a particular embodiment described therein, a cell-free broth containing a sulfate or phosphate salt of the amine (hence, e.g. DAB-disulfate) is concentrated, and a base, like ammonia is added. Depending on the conditions a two-layer system is formed. From the layer containing mainly the organic compounds, the desired amine can be recovered.

DETAILED DESCRIPTION OF THE INVENTION

According to one embodiment the method for the preparation of DAB involves at least one biocatalytic step, and comprises the steps of (a) biocatalytically preparing an N-protected precursor of DAB yielding a biocatalytic reaction mixture containing the N-protected precursor of DAB, (b) recovering the N-protected precursor from the biocatalytic reaction mixture, and (c) converting the N-protected precursor into DAB.

According to a particular embodiment the present invention for the production of DAB involves at least one biocatalytic step, which comprises the biocatalytic production of at least one N-protected precursor of DAB selected from the group consisting of $N^5$-protected ornithine, N-protected DAB, and N-protected 4-aminobutyraldehyde and subsequent in vitro conversion of the N-protected precursor into DAB.

With "in vitro conversion" is meant here conversion of an N-protected precursor of DAB into DAB in a medium outside a cell. The in vitro conversion can be a conversion by at least one biocatalyst or can be a chemical conversion involving at least one chemical step, or can be a combination of at least one biocatalytic and at least one chemical step.

With an "N-protected precursor of DAB" is meant here a compound containing a protected amino group and which can be converted into DAB by way of at least one chemical or biocatalytic reaction or a combination of chemical and biocatalytic reactions.

With "$N^5$-protected ornithine" is meant here the ornithine molecule which has a protecting group at its $N^5$ atom; with "N-protected DAB" is meant here the DAB molecule which has a protecting group at one of its amino groups; and with "N-protected 4-aminobutyraldehyde" is meant here the 4-aminobutyraldehyde molecule which has a protecting group at the amino group.

The protecting groups referred to above may be selected from the group consisting of acyl species having 1-6 carbon atoms or may be a guanidyl group. Such a protecting group should be selected to allow for at least one of biocatalytic production, ease of recovery of the N-protected precursor from the biocatalytic reaction mixture (e.g. fermentation broth) and subsequent biocatalytic and/or chemical reactions to ultimately produce DAB.

N-protected DAB precursors can be prepared by acylation of for example 4-aminobutyraldehyde or ornithine. For examples, by acylation with acetic acid anhydride in formic acid to introduce a formyl protecting group or by reaction of C2-C6 carboxylic acid anhydride or acyl chloride to introduce a N-acetyl, N-propionyl, N-butyryl, N-valeryl or N-caproyl protecting group, respectively.

N-guanidyl protected precursors are for example the proteinogenic arginine or N-guanidyl-aminobutyraldehyde or N-guanidyl-DAB. A fermentative route is described, for example, in EP1260588, which describes the biochemical production of agmatine from arginine under influence of an arginine decarboxylase. Agmatine is N-guanidyl-protected DAB. Agmatine (N-guanidyl-protected DAB) can be smoothly deprotected to DAB by acidic hydrolysis, for instance by refluxing agmatine in an aqueous concentrated mineral acid solution such as concentrated hydrochloric or sulfuric acid. This gives the diacid salt of DAB and the by-products carbon dioxide and ammonia (the latter in the form of its ammonium salt of the mineral acid which is used). To obtain the DAB in its free amine form, the formed diacid salt should be isolated, redissolved and neutralized with a base.

According to a further particular embodiment the invention relates to a method for the preparation of DAB wherein at least one N-protected precursor of DAB is produced, which N-protected precursor is selected from the group consisting of $N^5$-acetyl ornithine, N-acetyl DAB, and N-acetyl 4-aminobutyraldehyde.

According to one particular embodiment the method for the preparation of DAB involving at least one biocatalytic step comprises the steps of (a) biocatalytically preparing $N^5$-acetyl ornithine yielding a biocatalytic reaction mixture containing $N^5$-acetyl ornithine, (b) recovering $N^5$-acetyl ornithine from the biocatalytic reaction mixture, and (c) converting $N^5$-acetyl ornithine into DAB.

According to one particular embodiment the method for the preparation of DAB involving at least one biocatalytic step comprises the steps of (a) biocatalytically preparing N-acetyl DAB yielding a biocatalytic reaction mixture containing N-acetyl DAB, (b) recovering N-acetyl DAB from the biocatalytic reaction mixture, and (c) converting N-acetyl DAB into DAB.

According to one particular embodiment the method for the preparation of DAB involving at least one biocatalytic step comprises the steps of (a) biocatalytically preparing N-acetyl 4-aminobutyraldehyde yielding a biocatalytic reaction mixture containing N-acetyl 4-aminobutyraldehyde, (b) recovering N-acetyl 4-aminobutyraldehyde from the biocatalytic reaction mixture, and (c) converting N-acetyl 4-aminobutyraldehyde into DAB.

When referred herein explicitly or implicitly to an amine or an N-protected amine, e.g. N-protected DAB, these terms are meant to include the neutral amine group, the corresponding charged protonated amine as well as salts thereof.

DEFINITIONS

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

When referring to a compound of which stereoisomers exist, the compound may be any of such stereoisomers or a combination thereof. Thus, when referred to, e.g., an amino acid of which enantiomers exist, the amino acid may be the L-enantiomer or the D-enantiomer or a combination thereof. In case a natural stereoisomer exists, the compound is preferably a natural stereoisomer.

When an enzyme is mentioned with reference to an enzyme class (EC) between brackets, the enzyme class is a class wherein the enzyme is classified or may be classified on the basis of the Enzyme Nomenclature provided by the Nomenclature Committee of the International Union of Biochemistry and Molecular Biology (NC-IUBMB), which nomenclature may be found at http[colon][slash][slash]www[dot]chem[dot]qmul[dot]ac[dot]uk[slash]iubmb[slash]enzyme[slash]. Other suitable enzymes that have not (yet) been classified in a specified class but may be classified as such, are meant to be included.

The term "homologous" or "homolog" or "ortholog" refers to related sequences that have a functional relationship and is generally determined based on degree of sequence identity. These terms may describe the relationship between a gene found in one species, subspecies, variety, cultivar or strain and the corresponding or equivalent gene in another species, subspecies, variety, cultivar or strain. They may also describe the relationship between a gene found in nature and an artificially constructed gene, or between two artificially constructed genes. A functional relationship may be indicated in any one of a number of ways, including, but not limited to, (a) degree of sequence identity; (b) same or similar biological function. Preferably, both (a) and (b) are indicated. The term homolog is also meant to include nucleic acid sequences (polynucleotide sequences) which differ from another nucleic acid sequence due to the degeneracy of the genetic code and encode the same polypeptide sequence.

Wherever the term "homolog" is used herein in relation to a polypeptide, this is intended to indicate a polypeptide having the same or a similar biological function and a sequence identity of a certain degree with a reference polypeptide. In particular it is intended to indicate a sequence identity of at least 30%, preferably at least 40%, more preferably at least 60%, more preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%.

"Sequence identity" or "sequence similarity" is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., J. Mol. Biol. 1990, 215, 403-410, publicly available from NCBI and other sources (BLAST Manual, Altschul, S., et al., NCBI NLM NIH Bethesda, Md. 20894). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

With "biotransformation" or "biocatalytic reaction" is meant here a biochemical reaction wherein an enzyme is used as a catalyst. Wherever in accordance with the invention herein, it is indicated that a biocatalyst is used, at least one reaction step in the method is catalyzed by a biological material or moiety derived from a biological source, for instance an organism or a biomolecule derived there from. In particular, the biotransformation may be a fermentation step. The biocatalyst may in particular comprise one or more enzymes. The biocatalyst may be used in any form. In a particular embodiment, one or more enzymes are used isolated from the natural environment (isolated from the organism it has been produced in), for instance as a solution, an emulsion, a dispersion, (a suspension of) freeze-dried cells, as a lysate, or immobilized on a support. In an embodiment, one or more enzymes form part of a living organism (such as living whole cells). The enzymes may perform a catalytic function inside the cell. It is also possible that the enzyme may be secreted into a medium, wherein the cells are present.

With "biocatalytic reaction mixture" is meant here the environment in which the biocatalytic reaction takes place. This may be a cellular environment (for intracellular or extracellular biocatalytic reactions) or a cell-free environment.

With "fermentative step" is meant here a process step wherein the formation or conversion of a particular chemical entity takes place in a unicellular host, more in particular in a micro-organism in a cell culture. "Fermentatively preparing" means here producing a particular chemical entity in a micro-organism comprising a biocatalyst in a cell culture with a fermentable carbon source, wherein the carbon source contains any of said compounds which are to be converted into the particular chemical entity to be prepared or wherein the cells prepare the compound to be converted into the particular chemical entity to be prepared from the carbon source. The micro-organism may be a natural producer of the particular chemical entity or it may have obtained the capability to produce the particular chemical entity by transformation with a gene encoding at least one suitable enzyme using recombinant DNA techniques. The natural producer of the particular chemical entity may also be transformed with a gene encoding at least one suitable enzyme using recombinant DNA technology in order to increase the production of the desired particular chemical entity and/or to diminish the production of components which could interfere with the productivity of the desired particular chemical entity or which would interfere with the further steps in the process according to the present invention.

Preferred micro-organisms for fermentatively preparing the N-protected precursor of DAB may be of eukaryotic or prokaryotic origin. In particular it may be selected from animal (including human) cells, plant cells, bacteria, archaea, yeasts and fungi. More in particular the micro-organism may be selected from the group consisting of bacteria, such as *Bacillus* (in particular *B. subtilis*), *Brevibacterium* (in particular *B. ketoglutamicum*), corynebacteria (in particular *C. glutamicum*), *Escherichia* (in particular *E. coli*), *Klebsiella* (in particular *K. pneumoniae*), lactobacilli (in particular *L. lactis*), propionibacterium, pseudomonas (in particular *P. putida*), *Rodococcus* (in particular *R. erythropolis*, *Streptomyces* (in particular *S. coelicor* and *S. clavuligerus*), yeasts such as *Kluyveromyces* (in particular *K. lactis*), *Penicillium* (in particular *P. chrysogenum*), *Saccharomyces* (in particular *S. cerevisiae*), *Aspergillus* (in particular *A. niger*), *Pichia* (in particular *P. pastoris*), *Hansenula*, *Schizosaccharomyces* (in particular *S. pombe*), *Yarowia* (in particular *Y. lypolytica*), fungi, such as *Talaromyces*.

In the most preferred embodiment, the fermentative production of the N-protected precursor is performed in a micro-organism wherein the N-protected precursor is being formed in vivo. Preferably, the formation of the N-protected precursor according to the present invention is a biotransformation into the N-protected precursor from any suitable carbon source.

The carbon source for the fermentation process may in particular contain at least one compound selected from the group of monohydric alcohols, polyhydric alcohols, carboxylic acids, carbon dioxide, fatty acids, glycerides, including mixtures comprising any of said compounds. Suitable monohydric alcohols include methanol and ethanol, Suitable polyols include glycerol and carbohydrates. Suitable fatty acids or glycerides may in particular be provided in the form of edible oil, preferably of plant origin.

In particular a carbohydrate may be used, because usually carbohydrates can be obtained in large amounts from a biologically renewable source, such as an agricultural product, preferably an agricultural waste-material. Preferably a carbohydrate is used selected from the group of glucose, fructose, sucrose, lactose, saccharose, starch, cellulose and hemi-cellulose. Particularly preferred are glucose, oligosaccharides comprising glucose and polysaccharides comprising glucose.

Also, as a carbon source may be used amino acids or derivatives thereof, glutamate or derivatives thereof and/or ornithine or derivatives thereof.

As nitrogen source may be used inorganic nitrogen-containing compounds, such as ammonia, ammonia salts, ureum, nitrate and nitrite, or organic nitrogen-containing compounds, such as amino acids or derivatives thereof, more in particular glutamate or derivatives thereof and/or ornithine or derivatives thereof.

When reference is made here to a biocatalyst it may refer to an organism expressing at least one enzyme relevant for the biocatalytic function, or it may refer to at least one enzyme obtained or derived from an organism. The organism may be eukaryotic or prokaryotic. In particular the organism may be selected from animals (including humans), plants, bacteria, archaea, yeasts and fungi.

In one embodiment the biocatalyst originates from an animal, in particular from a part thereof—e.g. liver, pancreas, brain, kidney, heart or other organ. The animal may in particular be selected from the group of mammals, more in particular selected from the group of primates (like *Homo sapiens*), *Leporidae*, *Muridae*, *Suidae* and *Bovidae*.

Suitable plants as origin of the biocatalyst are, in particular, plants selected from the group of *Asplenium*; *Cucurbitaceae*, in particular *Cucurbita*, e.g. *Cucurbita moschata* (squash), or *Cucumis*; *Mercurialis*, e.g. *Mercurialis perennis*; *Hydnocarpus*; and *Ceratonia*.

Suitable bacteria as origin of the biocatalyst may in particular be selected amongst the group of *Acinetobacter*, *Agrobacterium*, *Alcaligenes*, *Bacillus*, *Brevibacterium*, *Clostridium*, *Corynebacterium*, *Deinococcus*, *Enterobacter*, *Enterococcus*, *Erwinia*, *Escherichia*, *Geobacillus*, *Klebsiella*, *Lactobacillus*, *Lactococcus*, *Legionella*, *Mycobacterium*, *Neisseria*, *Nitrosomonas*, *Novosphingobium*, *Paracoccus*, *Proteus*, *Pseudomonas*, *Ralstonia*, *Rhodobacter*, *Rhodopseudomonas*, *Salmonella*, *Shigella*, *Staphylococcus*, *Streptococcus*, *Streptomyces*, *Thermus*, *Vibrio* and *Zymomonas*.

Suitable archaea as origin of the biocatalyst may in particular be selected amongst the group of *Aeropyrum*, *Archaeoglobus*, *Halobacterium*, *Methanobacterium*, *Methanobrevibacter*, *Methanocaldococcus*, *Methanococcus*, *Methanopyrus*, *Methanosarcina*, *Methanosphaera*, *Pyrobaculum* and *Thermoplasma*.

Suitable fungi as origin of the biocatalyst may in particular be selected amongst the group of *Aspergillus*, *Neurospora*, *Penicillium*, *Rhizopus* and *Trichoderma*.

A suitable yeast as origin of the biocatalyst may in particular be selected amongst the group of *Candida*, *Cytophagia*, *Hansenula*, *Humicola*, *Kluyveromyces*, *Mucor*, *Rhizoctonia*, *Saccharomyces* and *Yarrowia*.

It will be clear to the person skilled in the art that use can be made of a naturally occurring biocatalyst (wild type) or a mutant of a naturally occurring biocatalyst with suitable activity in a method according to the invention. Properties of a naturally occurring biocatalyst may be improved by biological techniques known to the skilled person in the art, such as e.g. molecular evolution or rational design. Mutants of wild-type biocatalysts can for example be made by modifying the encoding DNA of an organism capable of acting as a biocatalyst or capable of producing a biocatalytic moiety (such as an enzyme) using mutagenesis techniques known to the person skilled in the art (random mutagenesis, site-directed mutagenesis, directed evolution, gene recombination, etc.). In particular the DNA may be modified such that it encodes an enzyme that differs by at least one amino acid from the wild-type enzyme, so that it encodes an enzyme that comprises one or more amino acid substitutions, deletions and/or insertions compared to the wild-type, or such that the mutants combine sequences of two or more parent enzymes or by effecting the expression of the thus modified DNA in a suitable (host) cell. The latter may be achieved by methods known to the skilled person in the art such as codon optimization or codon pair optimization, e.g. based on a method as described in WO 2008/000632.

A mutant biocatalyst may have improved properties, for instance with respect to one or more of the following aspects: selectivity towards the substrate, activity, stability, solvent tolerance, pH profile, temperature profile, substrate profile, susceptibility to inhibition, cofactor utilisation and substrate-affinity. Mutants with improved properties can be identified by applying e.g. suitable high through-put screening or selection methods based on such methods known to the skilled person in the art.

When referring to a biocatalyst, in particular an enzyme, from a particular source, recombinant biocatalysts, in particular enzymes, originating from a donor organism, but actually produced in a (genetically modified) host organism, are specifically meant to be included as biocatalysts, in particular enzymes, from that first organism.

Reaction conditions for any biocatalytic step in the context of the present invention may be chosen depending upon known conditions for the biocatalyst, in particular the enzyme, the information disclosed herein and optionally some routine experimentation.

The pH of the reaction medium used may be chosen within wide limits, as long as the biocatalyst is active under the pH conditions. Alkaline, neutral or acidic conditions may be used, depending on the biocatalyst and other factors. In case the method includes the use of a micro-organism, e.g. for expressing an enzyme catalyzing a method of the invention, the pH is selected such that the micro-organism is capable of performing its intended function or functions. The pH may in particular be chosen within the range of four pH units below neutral pH and two pH units above neutral pH, i.e. between pH 3 and pH 9 in case of an essentially aqueous system at 25° C. A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source) in such a concentration that micro-organisms which may be present remain active. In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

The incubation conditions can be chosen within wide limits as long as the biocatalyst shows sufficient activity and/or growth. This includes aerobic, micro-aerobic, oxygen limited and anaerobic conditions.

Anaerobic conditions are herein defined as conditions without any oxygen or in which substantially no oxygen is consumed by the biocatalyst, in particular a micro-organism, and usually corresponds to an oxygen consumption of less than 5 mmol/l·h, in particular to an oxygen consumption of less than 2.5 mmol/l·h, or less than 1 mmol/l·h.

Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen limited is dependent on the conditions under which the method is carried out, in particular by the amount and composition of ingoing gas flow, the actual mixing/mass transfer properties of the equipment used, the type of micro-organism used and the micro-organism density.

The temperature used is not critical, as long as the biocatalyst, in particular the enzyme, shows substantial activity. Generally, the temperature may be at least 0° C., in particular at least 15° C., more in particular at least 20° C. A desired maximum temperature depends upon the biocatalyst. In general such maximum temperature is known in the art, e.g. indicated in a product data sheet in case of a commercially available biocatalyst, or can be determined routinely based on common general knowledge and the information disclosed herein. The temperature is usually 90° C. or less, preferably 70° C. or less, in particular 50° C. or less, more in particular or 40° C. or less.

In particular if a biocatalytic reaction is performed outside a host organism, a reaction medium comprising an organic solvent may be used in a high concentration (e.g. more than 50%, or more than 90 wt. %), in case an enzyme is used that retains sufficient activity in such a medium.

In a preferred embodiment the present invention relates to a biocatalytic process whereby as an N-protected precursor of DAB $N^5$-protected ornithine is produced. For example, the preparation of $N^5$-acetyl ornithine may comprise one or more of the following enzyme-catalyzed reactions:
1) glutamate to N-acetyl-glutamate
2) N-acetyl-glutamate to N-acetyl-glutamate 5-phosphate
3) N-acetyl-glutamate 5-phosphate to N-acetyl-glutamate semialdehyde
4) N-acetyl-glutamate semialdehyde to $N^2$-acetyl-ornithine
5) $N^2$-acetyl-ornithine to $N^5$-acetyl-ornithine Reaction 1) may be catalyzed by an enzyme selected from the group of acyltransferases (EC 2.3.1), preferably from the group of amino-acid N-acetyltransferases (EC 2.3.1.1). Preferably, the enzyme is specific for acetyl-CoA as the acetyl-group donor and glutamate as the acetyl-group acceptor. An amino-acid N-acetyltransferase may originate from prokaryotes or eukaryotes. Exemplary proteins that can catalyze reaction 1) is given in Table 1 with their accession number in the Uniprot database and their source (micro)organisms.

Reaction 2) may be catalyzed by an enzyme selected from the group of acetyl-glutamate kinases (EC 2.7.2.8). The enzyme may use ATP as a cofactor. An acetyl-glutamate kinase may originate from prokaryotes or eukaryotes. Exemplary proteins that can catalyze reaction 2) is given in Table 1 with their accession number in Uniprot and their source (micro)organisms.

Reaction 3) may be catalyzed by an enzyme selected from the group of oxidoreductases (EC 1.2.1), preferably from the group of N-acetyl-gamma-glutamyl-phosphate reductases (EC 1.2.1.38). The enzyme may use NADH or NADPH as cofactor. An N-acetyl-gamma-glutamyl-phosphate reductase may originate from prokaryotes or eukaryotes. Exemplary proteins that can catalyze reaction 3) is given in Table 1 with their accession number in Uniprot and their source (micro) organisms.

Reaction 4) may be catalyzed by an enzyme selected from the group of transaminases (EC 2.6.1), preferably from the group of acetylornithine transaminases (EC 2.6.1.11). The enzyme may use glutamate as amino-group donor. An acetylornithine transaminase may originate from prokaryotes or eukaryotes. Exemplary proteins that can catalyze reaction 4) is given in Table 1 with their accession number in Uniprot and their source (micro)organisms.

Reaction 5) may be catalysed by an N-acyltransferase such as glutamate N-acetyltransferase (EC 2.3.1.35).

Glutamate may be derived from a suitable carbon source via glutamate biosynthesis reactions well known in the art. Preferably, microorganisms accumulating high amount of glutamic acid are used, for example, *Corynebacterium glutamicum*. Methods to improve glutamic acid production, for example by genetic engineering are well known in the art (Kimura E., Adv Biochem Eng Biotechnol. 2003; 79: 37-57).

Alternatively, the preparation of $N^5$-acetyl ornithine may comprise one or more of the following enzyme-catalyzed reactions:
6) glutamate to N-acetyl-glutamate
7) N-acetyl-glutamate plus ornithine to $N^2$-acetyl-ornithine
8) $N^2$-acetyl-ornithine to $N^5$-acetyl-ornithine

TABLE 1

Enzymes for reaction steps 1-8

| Reaction step | UniProt accession number | Enzyme | Microorganism |
|---|---|---|---|
| 1/6 | P0A6C5 | Amino-acid acetyltransferase | *Escherichia coli* |
| 1/6 | P40360 | Amino-acid acetyltransferase, mitochondrial | *Saccharomyces cerevisiae* |
| 2 | Q01217 | Protein ARG5,6, mitochondrial | *Saccharomyces cerevisiae* |
| 2 | P0A6C8 | Acetylglutamate kinase | *Escherichia coli* |
| 3 | Q01217 | Protein ARG5,6, mitochondrial | *Saccharomyces cerevisiae* |
| 3 | Q8ZKL8 | N-acetyl-gamma-glutamyl-phosphate reductase | *Salmonella typhimurium* |
| 4 | P18335 | Acetylornithine/succinyldiaminopimelate aminotransferase | *Escherichia coli* |
| 4 | P18544 | Acetylornithine aminotransferase | *Saccharomyces cerevisiae* |
| 5/7/8 | Q04728 | Arginine biosynthesis bifunctional protein ARG7, mitochondrial | *Saccharomyces cerevisiae* |
| 5/7/8 | Q9HW04 | Glutamate N-acetyltransferase | *Pseudomonas aeruginosa* |
| 5/7/8 | Q59280 | Glutamate N-acetyltransferase | *Corynebacterium glutamicum* |

Reaction 6) is identical to reaction 1) and can be catalyzed by the same type of enzymes.

Reaction 7) may be catalyzed by an enzyme selected from the group of acyltransferases (EC 2.3.1), preferably glutamate N-acetyltransferases (EC 2.3.1.35). Preferably, the enzyme uses ornithine as acetyl-group acceptor, thereby generating glutamate and N-acetyl-ornithine as reaction product. Glutamate N-acetyltransferases might have hydrolytic activity towards N-acetyl-glutamate, generating glutamate and acetate as hydrolysis products. Preferably, the enzyme used has no detectable hydrolytic activity; alternatively, a wild-type enzyme may be adapted such that the hydrolytic activity is substantially lower as compared to the wild type enzyme. A glutamate N-acetyltransferase may originate from prokaryotes or eukaryotes. Exemplary proteins that can catalyze reaction 7) is given in Table 1 with their accession number in Uniprot and their source (micro)organisms.

Reaction 8) is identical to reaction 5 and may be catalysed by the same enzyme.

In a further preferred embodiment the present invention relates to a biocatalytic process whereby N-protected DAB is produced from $N^5$-protected ornithine. In general, a suitable decarboxylase has $N^5$-protected ornithine decarboxylase activity, capable of catalysing the conversion of $N^5$-protected ornithine into N-protected DAB.

An enzyme capable of decarboxylating $N^5$-protected ornithine may in particular be selected from the group of decarboxylases (E.C. 4.1.1), preferably from the group of ornithine decarboxylases (EC 4.1.1.17), diaminopimelate decarboxylases (EC 4.1.1.20), branched chain alpha-keto acid decarboxylases (EC 4.1.1.72), alpha-ketoisovalerate decarboxylases, alpha-ketoglutarate decarboxylases (EC 4.1.1.71).

One or more other suitable decarboxylases may be selected amongst the group of oxalate decarboxylases (EC 4.1.1.2), acetoacetate decarboxylases (EC 4.1.1.4), valine decarboxylases/leucine decarboxylases (EC 4.1.1.14), aspartate 1-decarboxylases (EC 4.1.1.11), 3-hydroxyglutamate decarboxylases (EC 4.1.1.16), lysine decarboxylases (EC 4.1.1.18), arginine decarboxylases (EC 4.1.1.19), 2-oxoglutarate decarboxylases (EC 4.1.1.71), and diaminobutyrate decarboxylases (EC 4.1.1.86).

A decarboxylase may in particular be a decarboxylase of an organism selected from the group of squashes; cucumbers; yeasts; fungi, e.g. *Candida flareri, Hansenula* sp., *Kluyveromyces marxianus, Neurospora crassa, Rhizopus javanicus*, and *Saccharomyces cerevisiae*; mammals, in particular from mammalian brain; and bacteria, such as *Bacillus cadaveris, Escherichia coli, Lactococcus lactis, Mycobacterium tuberculosis, Pseudomonas* sp. and *Zymomonas mobilis*.

In a further preferred embodiment the invention relates to a biocatalytic process whereby N-protected DAB is produced through N-protected 4-aminobutyraldehyde. For example, the preparation of N-acetyl-DAB may comprise one or more of the following enzyme-catalyzed reactions:
9) glutamate to 4-aminobutyrate
10) 4-aminobutyrate to N-acetyl-4-aminobutyrate
11) N-acetyl-4-aminobutyrate to N-acetyl-4-aminobutyraldehyde
12) N-acetyl-4-aminobutyraldehyde to N-acetyl-DAB Reaction 9) may be catalyzed by an enzyme selected from the group of decarboxylases (EC 4.1.1), preferably from the group of glutamate decarboxylases (EC 4.1.1.15). A glutamate decarboxylase may originate from prokaryotes or eukaryotes or archaea.

Reaction 10) may be catalyzed by an enzyme selected from the group of acyltransferases (EC 2.3.1), preferably from the group of amino-acid N-acetyltransferases (EC 2.3.1.1), glycine N-acyltransferases (EC 2.3.1.13), aspartate N-acetyltransferases (EC 2.3.1.17), glutamate N-acetyltransferases (EC 2.3.1.35), D-amino-acid N-acetyltransferases (EC 2.3.1.36) and diamine N-acetyltransferases (EC 2.3.1.57). Preferably, the enzyme used is selective towards the substrate 4-aminobutyrate. The wild-type enzyme might have low activity/selectivity towards 4-aminobutyrate as amino-group acceptor. Such wild-type enzymes may be adapted such that the activity/selectivity towards 4-aminobutyrate is substantially higher as compared to the wild type enzyme. The enzyme used may use acetyl-CoA as acetyl-group donor. Alternatively, the enzyme may also use an N-acetylated amino acid as acetyl-group donor, such as N-acetyl-glutamate. The enzyme may originate from prokaryotes or eukaryotes or archaea.

Alternatively, N-acetyl-4-aminobutyrate can be converted to N-acetyl-4-aminobutyraldehyde by the following enzyme-catalyzed reactions:
11a) N-acetyl-4-aminobutyrate to N-acetyl-4-aminobutyrate phosphate
11b) N-acetyl-4-aminobutyrate phosphate to N-acetyl-4-aminobutyraldehyde Reaction 11a) may be catalyzed by an enzyme selected from the group of phosphotransferases (EC 2.7.2), preferably from the group of acetate kinases (EC 2.7.2.1), aspartate kinases (EC 2.7.2.4), butyrate kinases (EC 2.7.2.7), acetyl-glutamate kinases (2.7.2.8) and glutamate 5-kinases (2.7.2.11).

Reaction 11b) may be catalyzed by an enzyme selected from the group of oxidoreductases (EC 1.2.1), preferably from the group of N-acetyl-gamma-glutamyl-phosphate reductases (EC 1.2.1.38).

Exemplary proteins that can catalyze reaction steps 9) through 11) is given in Table 2 with their accession number in Uniprot and their source (micro)organisms.

TABLE 2

Enzymes for reaction steps 9-11(a/b)

| Reaction step | Uniprot accession | Enzyme | Microorganism |
|---|---|---|---|
| 9 | P69908 | Glutamate decarboxylase | E. coli |
| 9 | Q04792 | Glutamate decarboxylase | S. cerevisiae |
| 10 | P0A951 | Diamine acetyltransferase | E. coli |
| 10 | P21673 | Diamine acetyltransferase | H. sapiens |
| 10 | P41929 | Lysine acetyltransferase | Yarrowia lipolytica |
| 11 | P77674 | gamma-aminobutyraldehyde dehydrogenase | E. coli |
| 11a | P0A6C8 | acetylglutamate kinase | E. coli |
| 11b | P11446 | N-acetyl-gamma-glutamyl-phosphate reductase | E. coli |
| 11b | Q01217 | N-acetyl-gamma-glutamyl-phosphate reductase | S. cerevisiae |

Reaction 12) relates to a biocatalytic process whereby N-protected DAB is produced from N-protected 4-aminobutyraldehyde.

In general, a suitable aminotransferase has N-protected 4-aminobutyraldehyde aminotransferase activity, capable of catalysing the conversion of N-protected 4-aminobutyraldehyde to N-protected DAB.

The aminotransferase may in particular be selected amongst the group of aspartate aminotransferases, omega-aminotransferase (EC 2.6.1), classIII-aminotransferase (EC 2.6.1), 4-amino-butyrate aminotransferases (EC 2.6.1.19), L-lysine 6-aminotransferase (EC 2.6.1.36), 5-aminovalerate aminotransferases (EC 2.6.1.48), lysine:pyruvate 6-aminotransferases (EC 2.6.1.71) and putrescine-aminotransferase (EC 2.6.1.82).

In an embodiment an aminotransferase may be selected amongst the group of alanine aminotransferases (EC 2.6.1.2), leucine aminotransferases (EC 2.6.1.6), alanine-oxo-acid aminotransferases (EC 2.6.1.12), β-alanine-pyruvate aminotransferases (EC 2.6.1.18), (S)-3-amino-2-methylpropionate aminotransferases (EC 2.6.1.22), L,L-diaminopimelate aminotransferase (EC 2.6.1.83).

The aminotransferase may in particular be selected amongst aminotransferases from a mammal, plant or microorganism. More in particular, the aminotransferase may be derived from *Asplenium*, more in particular *Asplenium unilaterale* or *Asplenium septentrionale*, *Bacillus*, in particular *Bacillus weihenstephanensis*, *Bacillus cereus* and *Bacillus subtilis*, *Ceratonia*, more in particular *Ceratonia siliqua*, *Enterobacter*, *Erwinia*, more in particular *E. carotovora*, *Escherichia*, more in particular *E. coli*, *Legionella*, *Mercurialis*, in particular *Mercurialis perennis*, more in particular shoots of *Mercurialis perennis*, *Neisseria*, *Nitrosomonas*, *Pseudomonas*, in particular *Pseudomonas aeruginosa*, *Rhodobacter*, in particular *Rhodobacter sphaeroides*, *Rhodopseudomonas*, *Salmonella*, more in particular *S. typhi*, *S. paratyphi*, *Shigella*, more in particular *Sh. boydii*, *Sh. flexneri*, *S. sonnei*, *Staphylococcus*, in particular *Staphylococcus aureus*, *Vibrio*, in particular *Vibrio fluvialis*, or yeast, in particular *Saccharomyces cerevisiae*.

In case the enzyme is of a mammal, it may in particular originate from mammalian kidney, from mammalian liver, from mammalian heart or from mammalian brain. For instance a suitable enzyme may be selected amongst the group of 4-amino-butyrate aminotransferase from mammalian liver, in particular 4-amino-butyrate aminotransferase from pig liver; 4-amino-butyrate aminotransferase from mammalian brain, in particular 4-aminobutyrate aminotransferase from human, pig, or rat brain; omega-aminotransferase of *Vibrio fluvialis*, 4-amino-butyrate aminotransferase from *E. coli*, and 5-aminovalerate aminotransferase from *Clostridium* in particular from *Clostridium aminovalericum*.

In particular, the amino donor can be selected from the group of ammonia, ammonium ions, amines and amino acids. Suitable amines are primary amines and secondary amines. The amino acid may have a D- or L-configuration. Examples of amino donors are alanine, glutamate, isopropylamine, 2-aminobutane, 2-aminoheptane, phenylmethanamine, 1-phenyl-1-aminoethane, glutamine, tyrosine, phenylalanine, aspartate, alpha-aminoisobutyrate, beta-alanine, 4-aminobutyrate, and alpha-aminoadipate.

In a further preferred embodiment, the method for preparing N-protected DAB comprises a biocatalytic reaction in the presence of an enzyme capable of catalysing a reductive amination reaction in the presence of an ammonia source, selected from the group of oxidoreductases acting on the CH—$NH_2$ group of donors (EC 1.4), in particular from the group of amino acid dehydrogenases (E.C. 1.4.1). In general, a suitable amino acid dehydrogenase has 6-aminocaproic acid 6-dehydrogenase activity, catalysing the conversion of N-protected 4-aminobutyraldehyde to N-protected DAB. In particular a suitable amino acid dehydrogenase be selected amongst the group of diaminopimelate dehydrogenases (EC 1.4.1.16), lysine 6-dehydrogenases (EC 1.4.1.18), glutamate dehydrogenases (EC 1.4.1.3; EC 1.4.1.4), and leucine dehydrogenases (EC 1.4.1.9).

In an embodiment, an amino acid dehydrogenase may be selected amongst an amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), diaminopimelate dehydrogenases (EC 1.4.1.16), and lysine 6-dehydrogenases (EC 1.4.1.18).

An amino acid dehydrogenase may in particular originate from an organism selected from the group of *Corynebacterium*, in particular *Corynebacterium glutamicum*; *Proteus*, in particular *Proteus vulgaris*; *Agrobacterium*, in particular *Agrobacterium tumefaciens*; *Geobacillus*, in particular *Geobacillus stearothermophilus*; *Acinetobacter*, in particular *Acinetobacter* sp. ADP1; *Ralstonia*, in particular *Ralstonia solanacearum*; *Salmonella*, in particular *Salmonella typhimurium*; *Saccharomyces*, in particular *Saccharomyces cerevisiae*; *Brevibacterium*, in particular *Brevibacterium flavum*; and *Bacillus*, in particular *Bacillus sphaericus*, *Bacillus cereus* or *Bacillus subtilis*. For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; lysine 6-dehydrogenases from *Agrobacterium*, in particular *Agrobacterium tumefaciens*, lysine 6-dehydrogenases from *Geobacillus*, in particular from *Geobacillus stearothermophilus*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis*.

The biocatalytic enzyme may be used in any form. For example, the biocatalytic enzyme may be used—for example in the form of a dispersion, emulsion, a solution or in immobilized form (for instance loaded on a support, e.g. a particulate or monolithic carrier material)—as crude enzyme, as a commercially available enzyme, as an enzyme further purified from a commercially available preparation, as an enzyme obtained from its source by a combination of known purification methods, in whole (optionally permeabilised and/or immobilised) cells that naturally or through genetic modification possess hydrolytic activity, or in a lysate of cells with such activity.

The biocatalytic enzyme may be obtained or derived from any organism, in particular from an animal, plant, bacterium, a mould, a yeast or fungus.

It will be clear to the average person skilled in the art that use can also be made of mutants of naturally occurring (wild type) enzymes with biocatalytic activity in the process according to the invention. Mutants of wild-type enzymes can for example be made by modifying the DNA encoding the wild-type enzymes using mutagenesis techniques known to the person skilled in the art (random mutagenesis, site-directed mutagenesis, directed evolution, gene shuffling, etc.) so that the DNA encodes an enzyme that differs by at least one amino acid from the wild-type enzyme or so that it encodes an enzyme that is shorter compared to the wild-type and by effecting the expression of the thus modified DNA in a suitable (host) cell. Mutants of the biocatalytic enzyme may have improved properties, for instance with respect to one or more of the following aspects: selectivity towards the substrate, activity, stability, solvent resistance, pH profile, temperature profile, substrate profile.

When referring to an enzyme from a particular source, recombinant enzymes originating from a first organism, but actually produced in a (genetically modified) second organism, are specifically meant to be included as enzymes from that first organism.

A cell, in particular a recombinant cell, comprising one or more enzymes for catalysing one or several reaction step in a method of the invention can be constructed using molecular biological techniques, which are known in the art per se (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987). For instance, if one or more biocatalysts are to be produced in a recombinant cell (which may be a heterologous system), such techniques can be used to provide a vector (such as a recombinant vector) which comprises one or more genes encoding one or more of said biocatalysts. One or more vectors may be used, each comprising one or more of such genes. Such vector can comprise one or more regulatory elements, e.g. one or more promoters, which may be operably linked to a gene encoding an biocatalyst.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skilled in the art to act directly or indirectly to regulate the amount of transcription from the promoter. A "constitutive" promoter is a promoter that is active under most environmental and developmental conditions. An "inducible" promoter is a promoter that is active under environmental or developmental regulation. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The promoter that could be used to achieve the expression of the nucleic acid sequences coding for an enzyme for use in a method of the invention, in particular an aminotransferase, an amino acid dehydrogenase or a decarboxylase, such as described herein above may be native to the nucleic acid sequence coding for the enzyme to be expressed, or may be heterologous to the nucleic acid sequence (coding sequence) to which it is operably linked. Preferably, the promoter is homologous, i.e. endogenous to the host cell.

If a heterologous promoter (to the nucleic acid sequence encoding for the enzyme of interest) is used, the heterologous promoter is preferably capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters, which are well known to the person skilled in the art.

A "strong constitutive promoter" is one which causes mRNAs to be initiated at high frequency compared to a native host cell. Examples of such strong constitutive promoters in Gram-positive micro-organisms include SP01-26, SP01-15, veg, pyc (pyruvate carboxylase promoter), and amyE.

Examples of inducible promoters in Gram-positive micro-organisms include, the IPTG inducible Pspac promoter, the xylose inducible PxylA promoter.

Examples of constitutive and inducible promoters in Gram-negative microorganisms include, but are not limited to, tac, tet, trp-tet, lpp, lac, lpp-lac, laclq, T7, T5, T3, gal, trc, ara ($P_{BAD}$), SP6, $\lambda\text{-}P_R$, and $\lambda\text{-}P_L$.

Promoters for (filamentous) fungal cells are known in the art and can be, for example, the glucose-6-phosphate dehydrogenase gpdA promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, or another promoter, and can be found among others at the NCBI website http[colon][slash][slash]www[dot]ncbi[dot]nlm[dot]nih[dot]gov[slash]entrez[slash]).

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein.

A method according to the invention may be carried out in a host organism, which may be novel.

Accordingly, the invention also relates to a host cell comprising one or more enzymes capable of catalysing at least one reaction step in a method of the invention.

In a specific embodiment, a host cell according to the invention is a recombinant cell comprising a nucleic acid sequence encoding an enzyme capable of catalysing a transamination reaction or a reductive amination reaction to form $N^2$-protected ornithine from N-protected glutamate semialdehyde, or encoding an enzyme capable of catalyzing the N-acyltransferase reaction to form $N^5$-protected ornithine from $N^2$-protected ornithine, or encoding an enzyme capable of catalyzing the aminotransferase reaction to form N-protected DAB from N-protected 4-aminobutyraldehyde. Said sequence may be part of a vector or may have been inserted into the chromosomal DNA.

Recovery of N-Protected Precursor of DAB

Prior to conversion of the N-protected precursor into DAB, the N-protected precursor is to be recovered from the biocatalytic reaction mixture.

The recovery of the N-protected precursor from the biocatalytic reaction mixture can be carried out by methods known in the art for the recovery of similar chemical entities from a biocatalytic reaction mixture. In particular for a fermentative production process such a recovery process may comprise at least one step selected from the group consisting of cell separation (filtration, membrane separation (MF), sedimentation (as gravity and centrifugal), crystallization, to remove the cells. A further concentration and purification of N-protected precursor may be required for economical favorable purification. For further concentration, techniques as evaporation and membrane separation (RO, NF and UF) can be applied. Also techniques as (eutectic) freeze concentration can be used.

Further isolation may be necessary either by ion-exchange (chromatography) or by crystallization/precipitation This process should not necessarily result in meticulous purification of the N-protected precursor, but the N-protected precursor should be purified to at least such an extent that subsequent conversion of the N-protected precursor into DAB will not substantially be hampered by contaminants and side products originating from the biocatalytic reaction mixture. Optionally, the N-protected precursor also may be concentrated.

Furthermore, the N-protected precursor may be transferred to a medium which is optimized for the at least one subsequent transformation step.

Conversion of N-Protected Precursor of DAB to DAB

The direct or indirect conversion of the N-protected precursor into DAB according to present invention may involve at least one biocatalytic (in particular enzymatic) or chemical conversion step. It may also involve a combination of biocatalytic and chemical conversion steps.

For example, the conversion of biocatalytically produced N-protected DAB into unprotected DAB may be carried out by a biocatalytic or a chemical hydrolytic process. For the biocatalytic process use can be made of a suitable hydrolase. In an advantageous method of the invention, the deacylation is biocatalysed. In particular use may be made of a hydrolytic enzyme capable of catalysing the deacylation of N-Ac-DAB, more in particular capable of catalysing the deacetylation of N-acetyl-DAB.

When N-acetyl-DAB is converted to DAB by either chemical or biocatalytic hydrolysis, this generally leads to the formation of both DAB and acetate. After recovery of DAB, the acetate containing part is preferably reused in the process. In case of a fermentative process the acetate may be reused as a carbon source to grow the microorganism, or, as a carbon source to produce the N-protected-DAB or a compound which can be converted into N-protected DAB in the fermentation process.

The term 'hydrolytic enzyme' is used herein for enzymes from the classification group E.C. 3. Preferably, one or more hydrolytic enzymes are used selected from the group of carboxylic ester hydrolases (E.C. 3.1.1), thiolester hydrolases (E.C. 3.1.2) and peptidases (E.C. 3.4).

In particular a peptidase (E.C. 3.4) may be used. Preferred peptidases are peptidases selected from the group of serine-type carboxypeptidases (E.C. 3.4.16), metallocarboxypeptidases (E.C. 3.4.17), cysteine-type carboxypeptidases (E.C. 3.4.18), serine endopeptidases (E.C. 3.4.21), cysteine endopeptidases (E.C. 3.4.22), aspartic endopeptidases (E.C. 3.4.23) and metalloendopeptidases (E.C. 3.4.24), in particular from serine endopeptidases (E.C. 3.4.21). In particular good results have been achieved with a serine endopeptidase, preferably subtilisin (E.C. 3.4.21.62), such as subtilisin Carlsberg.

Examples of organisms from which the hydrolytic enzyme may be derived include *Trichoderma* sp, such as from *Trichoderma reesei; Rhizopus* sp., such as from *Rhizopus oryzae; Bacillus* sp, such as from *Baccillus licheniformis, Bacillus subtilis, Bacillus amyloliquefaciens, Bacillus clausii, Bacillus lentus, Bacillus alkalophilus, Bacillus halodurans; Aspergillus* sp., such as from *Aspergillus oryzae* or *Aspergillus niger, Streptomyces* sp., such as from *caespitosus Strep-* tomyces or *Streptomyces griseus; Candida* sp.; fungi; *Humicola* sp; *Rhizoctonia* sp.; *Cytophagia; Mucor* sp.; and animal tissue, in particular from pancreas, such as from porcine pancreas, bovine pancreas or sheep pancreas.

As indicated above, a preferred enzyme is subtilisin. Various subtilisins are known in the art, see e.g. U.S. Pat. No. 5,316,935 and the references cited therein. Subtilisin A is a commercially available subtilisin from Novozymes. Particularly preferred is subtilisin Carlsberg. Alcalase® has been found to be particularly suitable for use in a method of the invention. This product is available from Novozymes (Bagsvaerd, Denmark). Alcalase® is a cheap and industrially available proteolytic enzyme mixture produced by *Bacillus licheniformis* (containing subtilisin Carlsberg as a major enzyme component). Experiments with purified subtilisin confirmed that subtilisin catalyses transesterification, activation and peptidic bond formation.

Novozymes (Bagsvaerd, Denmark) offers ovozyme, liquanase, Alcalase®, Alcalase-ultra® (in particular effective at alkaline pH), duramyl, esperase, kannase, savinase, savinase ultra, termamyl, termamyl ultra, novobate, polarzyme, neutrase, novoline, pyrase, novocor (bacterial alkaline proteases).

Proteinase-K is available from New England Biolabs, Ipswich (MA), USA).

Novo Nordisk Biochem North America Inc (Franklinton N.C., USA) offers Protease *Bacillus* species (Esperase 6.0 T; Savinase 6.0 T), Protease *Bacillus subtilis* (Neutrase 1.5 MG), Protease *Bacillus licheniformis* (Alcalase 3.0 T).

Amano International Enzyme Co (Troy, Va., USA) offers Protease *Bacillus subtilis* (Proleather; Protease N) and Protease *Aspergillus oryzae* (Prozyme 6).

Suitable examples of this class of enzymes are e.g. *Rhizopus japonicus* lipase, lipase AP-6 of *Aspergillus niger*, lipase QL of *Alcaligenes* sp, protease B of *Bacillus amyloliquefaciens* (SEQ ID NO:19), Delvolase of *Bacillus licheniformis* (SEQ ID NO: 20), *Rhizopus oryzae* lipase, Esperase, Alcalase, *Aspergillus* species acylase, Prozyme, Protease M, Protease N. The hydrolase preferably is selected from the group of hydrolases acting on ester bonds (lipases, esterases) (EC 3.1), peptide hydrolases acting on peptide bonds (peptidase, proteinases) (EC 3.4), and hydrolases acting on C—N bonds other than peptide bonds (EC 3.5).

In particular a hydrolase acting on C—N bonds other than peptide bonds may be selected from the group of carboxylic ester hydrolases (EC 3.1.1) and amidases acting on linear amides (EC 3.5.1), specifically from the group of amino amidases, more specifically from the group of amino amidases from *Mycobacterium*, more specifically amino amidases from *Mycobacterium neoaurum*.

The chemical hydrolysis of the N-protected DAB may comprise a process known in the art for similar reactions. A suitable method involves deacylation by a $(PhO)_3P.Cl_2$ reagent prepared in situ by titrating a solution of triphenyl phosphate with chlorine. This method is generally described by Saggiari et al (Organic Letters (2004), 6 (22), pp. 3885-3888.

The conversion of $N^5$-protected ornithine into unprotected DAB may proceed by first specifically decarboxylating the $N^5$-protected ornithine to result into N-protected DAB and subsequently hydrolyzing N-protected DAB to yield unprotected DAB as described before.

For the specific decarboxylation of $N^5$-protected ornithine to result into N-protected DAB use may be made of a suitable biocatalyst, such as an enzyme with lyase activity. Suitable enzymes with lyase activity belong to class EC 4. More in particular use can be made of carbon-carbon lyases (EC 4.1) such as carboxylases (EC 4.1.1) as exemplified by ornithine decarboxylase (SpeC) of *Escherichia coli* (EC 4.1.1.17), branched chain alpha-ketoacid decarboxylase (KdcA; SEQ ID NO:8 (amino acid SEQ ID NO:9)) and alpha-ketoisovalerate decarboxylase (KivD; SEQ ID NO:10 (amino acid SEQ ID NO:11)) of *Lactococcus lactis* and lysine decarboxylase (LysA; SEQ ID NO:12 (amino acid SEQ ID NO:13) of *Escherichia coli*.

Alternatively, the first mentioned specific decarboxylation of $N^5$-protected ornithine may be carried out by a chemical conversion known in the art for similar chemical entities. Suitable chemical decarboxylation reactions for this purpose can be done by heating the compound in a high boiling solvent, such as diphenylmethane, optionally in the presence of a catalytic amount of an organic peroxide, or may be done by heating the compound with one or more equivalents of a ketone or aldehyde.

The subsequent hydrolysis of N-protected DAB may be performed by a biocatalytic or a chemical process as described above for the biocatalytically produced N-protected DAB.

As an alternative for the two-step conversion described above, use can be made of a one-pot process to produce DAB from $N^5$-protected ornithine. This process may proceed by either first deacylating the $N^5$-protected ornithine and subsequent decarboxylation, or by first decarboxylating $N^5$-protected ornithine and subsequent deacylation according to methods known in the art for similar compounds. Decarboxylation can be done as described above. Deacylation can be done by the method described above for N-protected DAB.

The conversion of N-protected 4-aminobutyraldehyde into unprotected DAB may proceed by first specifically replacing the aldehyde oxygen by an amino group, thereby forming N-protected DAB, and subsequently de-protecting the latter. For the first conversion use may be made of a suitable biocatalyst, such as an enzyme with transferase activity (EC 2) as described before. Suitable enzymes with transferase activity for this particular purpose are exemplified by the transferases transferring nitrogenous groups (EC 2.6), more in particular aminotransferases (transaminases) (EC 2.6.1), further in particular 4-amino-butyrate aminotransferase from mammalian liver, more in particular 4-amino-butyrate aminotransferase from pig liver; 4-amino-butyrate aminotransferase from mammalian brain, more in particular 4-aminobutyrate aminotransferase from human, pig, or rat brain; omega-aminotransferase of *Vibrio fluvialis*, 4-amino-butyrate aminotransferase from *E. coli*, and 5-aminovalerate aminotransferase from *Clostridium*, more in particular from *Clostridium aminovalericum*, ornithinetransaminase (EC 2.6.1.11), L-alanine:3-oxopropionate aminotransferase (EC 2.6.2.18) and putrescine amino transferase of e.g. *Shigella* or *Salmonella*. Particularly suitable aminotransferases are e.g. omega-aminotransferase of *Vibrio fluvialis* (SEQ ID NO:5), or aminotransferases of *Pseudomonas aeruginosa* (gi9946143 (SEQ ID NO:1) or gi9951072 (SEQ ID NO:3)), *Paracoccus denitrificans* (ZP00628577; SEQ ID NO:14), *Bacillus weihenstephanensis* (ZP01186960 (SEQ ID NO:16)).

Other suitable biocatalysts for the conversion of N-protected 4-aminobutyraldehyde into N-protected DAB are enzymes with oxidoreductases (EC 1), more in particular oxidoreductases acting on CH—$NH_2$ groups (EC 1.4) or CH—NH groups (EC 1.5) of donors, and more in particular enzymes of the classes EC 1.4.1, 1.4.3 (preferably 1.4.3.4) and 1.4.99.

Alternatively the first conversion of N-protected 4-aminobutyraldehyde may be carried out by a chemical conversion known in the art for similar chemical entities. Suitable chemical reactions for this purpose can be executed by a reductive amination of N-protected 4-aminobutyraldehyde according to methods known in the art for similar compounds (see e.g. DE 4322065). A suitable method is for example reaction with ammonia and hydrogen over a heterogeneous catalyst (such as RaNi, Ni/SiO$_2$ and or Al$_2$O$_3$, Ru/C, Rh/C) or a homogeneous catalyst (such as a homogeneous Rh catalyst).

The subsequent hydrolysis of N-protected DAB may be performed by a biocatalytic or a chemical process as described above for the biocatalytically produced N-protected DAB.

DESCRIPTION OF THE FIGURES

FIG. 1. TLC of the end time sample of the bioconversion of N-Ac-Ornithine towards N-Ac-DAB. 1) Glutamate DC; 2) Aspartate DC; 3) LysA; 4) KdcA; 5) KivD; 6) Kgd; 7) Lysin DC; 8) ODC LJ110; 9) ODC DH5α; 10) enzyme blank; 11) Chemical blank; 12) N-Ac-Ornithine reference sample; 13) N-Ac-DAB reference sample; 14) N-Ac-Ornithine & N-Ac-DAB reference sample.

EXAMPLES

General Methods

Molecular and Genetic Techniques

Standard genetic and molecular biology techniques are generally known in the art and have been previously described (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987).

Plasmids and Strains pBAD/Myc-His C was obtained from Invitrogen (Carlsbad, Calif., USA). Plasmid pBAD/Myc-His-DEST constructed as described in WO2005/068643, was used for protein expression. E. coli TOP10 (Invitrogen, Carlsbad, Calif., USA) was used for all cloning procedures and for expression of target genes.

Media

LB medium (10 g/l tryptone, 5 g/l yeast extract, 5 g/l NaCl) was used for growth of E. coli. Antibiotics (50 µg/ml carbenicillin) were supplemented to maintain plasmids. For induction of gene expression under control of the P$_{BAD}$ promoter in pBAD/Myc-His-DEST derived plasmids, L-arabinose was added to a final concentration of 0.2% (w/v).

Production of Amino Amidase of M. neoaurum

Amino amidase was obtained by growth of Mycobacterium neoaurum strain ATCC 25795 under following conditions. One liter of Mycomed medium containing 4.8 g/l nitrilotriacetic acid (NTA), 4 g/l urea, 6 g/l glucose, 20 g/l yeast carbon base (YCB from Difco), 1.55 g/l K$_2$HPO$_4$ and 0.85 g/l NaH$_2$PO$_4$.H$_2$O were adjusted to pH 7 and inoculated with a glycerol stock culture of Mycobacterium neoaurum strain ATCC 25795. The preculture was shaken on a New Brunswick Scientific G53 shaker (150 rpm, amplitude 4 cm) at 37° C. for 168 hours. When an optical density (OD$_{620}$ nm) of 3.45 was reached, 500 ml of the preculture was used to inoculate 9 l of Mycomed medium. Amidase expression was induced by NTA present in the Mycomed medium. The fermentation culture was stirred at 375-750 rpm at an aeration rate of 0.5-2 l/min. The pH was kept constant at 7 by addition of H$_3$PO$_4$ and NaOH. The cultivation temperature was 37° C. After 44 hours of cultivation, the culture was fed by addition of 10 g/l YCB. After 68 hours of cultivation, the culture was fed by addition of 10 g/l glucose. After 94 hours of cultivation, the culture was harvested by centrifugation at 12,000 g for 10 minutes. The cell pellet was washed in 20 mM HEPES/NaOH buffer, pH 7 and subsequently freeze-dried for storage.

Identification of Plasmids

Plasmids carrying the different genes were identified by genetic, biochemical, and/or phenotypic means generally known in the art, such as resistance of transformants to antibiotics, PCR diagnostic analysis of transformant or purification of plasmid DNA, restriction analysis of the purified plasmid DNA or DNA sequence analysis.

Cloning of Target Genes

Design of Expression Constructs attB sites were added to all genes upstream of the ribosomal binding site and start codon and downstream of the stop codon to facilitate cloning using the Gateway technology (Invitrogen, Carlsbad, Calif., USA).

Gene Synthesis and Construction of Plasmids

Synthetic genes were obtained from DNA2.0 and codon optimised for expression in E. coli according to standard procedures of DNA2.0. The aminotransferase genes from Vibrio fluvialis [SEQ ID NO:5] and Bacillus weihenstephanensis KBAB4 [SEQ ID NO:16] encoding the amino acid sequences of the V. fluvialis JS17 omega-aminotransferase [SEQ ID NO:6] and the B. weihenstephanensis KBAB4 aminotransferase (ZP_01186960) [SEQ ID NO:17], respectively, were codon optimised and the resulting sequences [SEQ ID NO:7] and [SEQ ID NO:18] were obtained by DNA synthesis.

The gene constructs were cloned into pBAD/Myc-His-DEST expression vectors using the Gateway technology (Invitrogen) via the introduced attB sites and pDONR201 (Invitrogen) as entry vector as described in the manufacturer's protocols (www.invitrogen.com). This way the expression vectors pBAD-Vfl_AT and pBAD-Bwe_AT were obtained, respectively. The corresponding expression strains were obtained by transformation of chemically competent E. coli TOP10 (Invitrogen) with the respective pBAD-expression vectors.

In a similar way, an expression vector was made with the aminotransferase gene from Paracoccus denitrificans [SEQ ID NO:14] encoding the amino acid sequence of SEQ ID NO:15.

Cloning by PCR

The aminotransferase genes were amplified from genomic DNA by PCR using PCR Supermix High Fidelity (Invitrogen) according to the manufacturer's specifications, using primers as listed in Table 3.

TABLE 3

| Origin of gene | Gene SEQ ID NO: | Enzyme SEQ ID NO: | Forward primer SEQ ID NO: | Reverse primer SEQ ID NO: |
|---|---|---|---|---|
| Pseudomonas aeruginosa gi9946143 | 1 | 2 | 23 | 24 |
| Pseudomonas aeruginosa gi9951072 | 3 | 4 | 25 | 26 |

PCR reactions were analyzed by agarose gel electrophoresis and PCR products of the correct size were eluted from the gel using the QIAquick PCR purification kit (Qiagen, Hilden, Germany). Purified PCR products were cloned into pBAD/Myc-His-DEST expression vectors using the Gateway technology (Invitrogen) via the introduced attB sites and pDONR-zeo (Invitrogen) as entry vector as described in the manufacturer's protocols. The sequence of genes cloned by PCR was verified by DNA sequencing. This way the expression vectors pBAD-Pae-_gi9946143_AT, pBAD-Pae_gi9951072_AT and pBAD-Pde_AT_ZP00628577 were obtained. The corresponding expression strains were obtained by transformation of chemically competent *E. coli* TOP10 (Invitrogen) with the pBAD constructs.

Growth of *E. coli* for Protein Expression

Small scale growth was carried out in 96-deep-well plates with 940 μl media containing 0.02% (w/v) L-arabinose. Inoculation was performed by transferring cells from frozen stock cultures with a 96-well stamp (Kühner, Birsfelden, Switzerland). Plates were incubated on an orbital shaker (300 rpm, 5 cm amplitude) at 25° C. for 48 h. Typically an $OD_{620nm}$ of 2-4 was reached.

Preparation of Cell Lysates

Preparation of Lysis Buffer

The lysis buffer contained the ingredients listed in table 4:

TABLE 4

| | |
|---|---|
| 1M MOPS pH 7.5 | 5 ml |
| DNAse I grade II (Roche) | 10 mg |
| Lysozyme | 200 mg |
| $MgSO_4 \cdot 7H_2O$ | 123.2 mg |
| dithiothreitol (DTT) | 154.2 mg |
| $H_2O$ (MilliQ) | Balance to 100 ml |

The solution was freshly prepared directly before use.

Preparation of Cell Free Extract by Lysis

Cells from small scales growth (see previous paragraph) were harvested by centrifugation and the supernatant was discarded. The cell pellets formed during centrifugation were frozen at −20° C. for at least 16 h and then thawed on ice. 500 μl of freshly prepared lysis buffer were added to each well and cells were resuspended by vigorously vortexing the plate for 2-5 min. To achieve lysis, the plate was incubated at room temperature for 30 min. To remove cell debris, the plate was centrifuged at 4° C. and 6000 g for 20 min. The supernatant was transferred to a fresh plate and kept on ice until further use.

Preparation of Cell Free Extract by Sonification

Cells from medium scales growth (see previous paragraph) were harvested by centrifugation and the supernatant was discarded. 1 ml of potassium phosphate buffer pH7 was added to 0.5 g of wet cell pellet and cells were resuspended by vigorously vortexing. To achieve lysis, the cells were sonicated for 20 min. To remove cell debris, the lysates were centrifuged at 4° C. and 6000 g for 20 min. The supernatant was transferred to a fresh tube and frozen at −20° C. until further use.

Bioconversion of N-acetyl-4-aminobutyraldehyde to N-acetyl-DAB

Screening Conditions

All enzymes were suspended in 100 mM potassium phosphate buffer pH 7.5 to a final volume of 100 μl. The enzymatic reactions were started by addition of 150 μl of a stock solution containing the amine donor (L-alanine or (S)-alpha methylbenzylamine) and cofactor (PLP). The final concentrations in the 250 μl reaction mixture were: N-acetyl-aminobutanal (70 mM), amine donor (140 mM), PLP (12.5 mM). The two amine donors were tested separately. The reaction mixtures were incubated overnight (16.5 and 16 hours) at 28° C., while shaking at 560 rpm on an IKA orbital shaker. After incubation, the reaction mixtures were stopped and diluted by addition of 750 μl 60% dilution of acetonitril with 0.2% formic acid. The microtiterplates were centrifuged at 3500 rpm for 20 minutes. Analysis was performed by means of LC-MS analysis (see Resolve Job 2009-02-00649).

Analytical Methods:

In total, 148 samples were analyzed by means of LC-MS, using the analytical method described in job 2009-01-00306. Detection limit; linear range: for amine donor L-alanine 0 μmol/L-550 μmol/L and for amine donor (S)-alpha methylbenzylamine 0 μmol/L-280 μmol/L.

Results of bioconversion of N-acetyl-4-aminobutyraldehyde into N-acetyl-DAB

In total 148 transaminase enzymes were screened for the route of N-acetyl-4-aminobutyraldehyde towards N-acetyl-DAB. All samples have been analyzed by means of LC-MS for conversion. The conversions were calculated based on the formation of N-acetyl-DAB. In total, 31 aminotransferase hits (>2% conv.) were found when using L-alanine as amine donor. 20 of these were also positive when using (S)-α-methyl benzylamine as amine donor. Five of these positive hits are exemplified in Table 5.

TABLE 5

Hits showing >2% conversion in the bioconversion of N-acetyl-4-aminobutyraldehyde into N-acetyl-DAB

| Enzyme/origin | Orf/insert | platform |
|---|---|---|
| *Vibrio fluvialis* JS17 | clone | SdW/RS AT3 |
| *Pseudomonas aeruginosa* | Pae_AT_gi9946143 | SPEED TA 1 |
| *Pseudomonas aeruginosa* | Pae_AT_gi9951072 | SPEED TA 1 |
| *Paracoccus denitrificans* | Pde_AT_ZP00628577 | SdW/RS AT3 |
| *Bacillus weihenstephanesis* | Bwe_AT_ZP01186960 | SdW/RS AT3 |

Bioconversion of N-Acetyl-DAB into DAB.

Screening Conditions

All enzymes were suspended in a final volume of 100 μl of 100 mM potassium phosphate at pH 7.5. The enzymatic reactions were started by addition of 150 μl of a 13.33 mg/ml N-acetyl-DAB.HCl in potassium phosphate buffer 100 mM (final reaction concentration of 8 mg/ml≈48 mM N-acetyl-DAB). The reaction mixtures were incubated overnight at 37° C., while shaking at 460 rpm on an IKA orbital shaker. After incubation, the reaction mixtures were stopped and diluted by addition of 750 μl 100 mM $HClO_4$ in $H_2O$, pH 1.0. The microtiter plates were centrifuged at 3500 rpm for 20 minutes and analyzed for DAB by means of HPLC-PCR-FL analysis as described below.

HPLC-MS Analysis Method for the Determination of DAB

Sample Preparation:

A mixture of acetonitrile and water with 0.2% of formic acid is used to dilute the sample. The percentage of acetonitrile must be at least 50%

LC Conditions:

| | |
|---|---|
| Column | 50 × 4.6 mm, HP HILIC, 3 μm (Alltech) |
| Column temperature | room temperature (24° C.) |
| Eluent | A: acetonitrile containing 0.2% formic acid |
| | B: water containing 0.2% formic acid |

| | time (min) | % eluent B |
|---|---|---|
| Gradient | 0 | 5 |
| | 2.5 | 20 |
| | 10 | 20 |
| | 11.1 | 5 |
| | 15 | 5 |

-continued

| Flow | 1 ml/min, before entering the MS the flow is split 1:5 |
| --- | --- |
| Injection volume | 2 μl |

MS Conditions:

| Ionisation | positive ion turbo ionspray source conditions | ionspray voltage: 5 kV temperature: 400° C. defragmentation potential: 51 V focusing potential: 180 V |
| --- | --- | --- |
| Scan mode (DAB) | selective ion mode | m/z 72 (dwell time 200 msec) |

Under the applied conditions DAB elutes at 6.3 minutes

Results of Bioconversion of N-Acetyl-DAB to DAB

A selection from the enzymes tested, which showed hydrolytic activity in the bioconversion of N-acetyl-DAB to DAB are listed in table 6. A few of these enzymes are also characterized by their sequence information incorporated into this patent application.

TABLE 6

Hydrolysis of N-acetyl-DAB to DAB (SEQ ID NO: 22 is the amino acid sequence of SEQ ID NO: 21)

| Biocatalyst | Supplier | Concentration DAB (μM) | SEQ ID NO: | Uniprot No |
| --- | --- | --- | --- | --- |
| Rhizopus japonicus lipase | Biocatalysts LTD | 690 | | |
| Aspergillus niger lipase (lipase AP-6) | Amano | 278 | | |
| Alcaligenes sp. lipase (lipase QL) | Meito Sangyo | 186 | | |
| Bacillus amyloliquefaciens protease (protease B) | DSM-Gist | 142 | 19 | |
| Bacillus licheniformis protease (Delvolase) | DSM-Gist | 162 | 20 | |
| Rhizopus oryzae lipase | DSM-Gist | 1846 | | P61872 |
| Esperase | NOVO | 158 | | |
| Alcalase | NOVO | 130 | | |
| Aspergillus species (Acylase) | Sigma | 270 | | |
| Prozyme 6 | Amano | 346 | | |
| Protease M | Amano | 206 | | |
| Bacillus subtilis (Protease N) | Amano | 514 | | |
| Mycobacterium neoaurum L-amino amidase | DSM | 1174 | | |
| Cerdase | Novozymes | 530 | 21 | |
| chem blank | | 108 | | |
| chem blank | | 104 | | |

CONCLUSION

A large number of hydrolytic enzymes were found to be useful as biocatalyst for the conversion of N-acetyl-DAB to DAB.

N-protected DAB precursors with other acyl-protecting groups can be prepared by acylation of for example 4-aminobutyraldehyde or ornithine. For examples, by acylation with acetic acid anhydride in formic acid to introduce a formyl protecting group or by reaction of C2-C6 carboxylic acid anhydride or acyl chloride to introduce a N-acetyl, N-propionyl, N-butyryl, N-valeryl or N-caproyl protecting group, respectively. It is anticipated that these N-protected DAB precursors such as N-formyl-DAB, and the higher homologues with C3-C6 acyl protecting groups, can be converted analogously by the enzymes described above.

Bio Conversion of $N^5$-Acetyl-Ornithine into N-Acetyl-DAB

Cell Cultivation and Expression

This bioconversion was made with decarboxylases. Most of the decarboxylases were expressed in E. coli under standard condition.

Precultures were made by inoculation of 5 ml $LB^{carb}$ medium with E. coli Top10 harbouring pBAD-DEST_lysA, pBAD-DEST_kdcA, pBAD-DEST_kivD or pBAD-DEST_kgd from glycerol stocks. The precultures were incubated overnight at 28° C. 0.5 ml of each preculture was diluted out in 50 ml $LB^{carb}$ medium. The cultures were incubated at 28° C. until an $OD_{600}$ of 0.6 was reached (on average after 3-4 hrs). Protein expression was induced by adding arabinose to a final concentration of 0.02%. After overnight incubation at 28° C. the cells were harvested (10 min, 5000 rpm, 4° C.). For analysis with SDS-PAGE 1 ml samples were taken before induction, 3 hours after induction and overnight. The cells were pelleted (5 min, 13,000 rpm) and the pellet was stored at −20° C.

The two ornithine decarboxylases pBAD2_ODC E. coli DH5α/LJ110 were grown and expressed under slightly different conditions. Here the main culture was grown to an $OD_{620}$ of 1.5 before inducing with 50 μM IPTG. All other conditions were the same as described above.

CFE Preparation by Sonification

Cell pellets were thawed on ice and resuspended in 2 volumes 50 mM kalium-phosphate (KPi) buffer pH 7.5. The cell suspensions were sonificated for 10 minutes with pulses for 10 seconds on and off. After sonification cell debris was pelleted by centrifugation (20 min, 13,200 rpm, 4° C.). SDS-PAGE analysis was used to determine the expression levels and the CFE's were stored at −20° C.

TABLE 7

Bioconversion conditions for the conversion of N—Ac-omithine towards N—Ac-DAB\

| Reaction | 200 mM K-acetate pH 4.6 | 200 mM KP pH 6.9 | 200 mM KP pH 7.5 | 200 mM KP pH 6.5 | 100 mM K-acetate pH 5.7 | 200 mM N—Ac-Ornithine | 10 mM PLP | 100 mM ThD | 4M NaCl | 50 mM EDTA | 1M MgCl2 | Enzyme | Water | Total |
| --- | --- | --- | --- | --- | --- | --- | --- | --- | --- | --- | --- | --- | --- | --- |
| Glutamate DC A | 1.875 | | | | | 1.25 | 0.05 | | 0.25 | | | 1 | 0.575 | 5 |
| Aspartate DC A | | | 1.875 | | | 1.25 | 0.05 | | | 0.5 | | 1 | 0.325 | 5 |

TABLE 7-continued

Bioconversion conditions for the conversion of N—Ac-ornithine towards N—Ac-DAB\

| Reaction | 200 mM K-acetate pH 4.6 | 200 mM KP pH 6.9 | 200 mM KP pH 7.5 | 200 mM KP pH 6.5 | 100 mM K-acetate pH 5.7 | 200 mM N—Ac-Ornithine | 10 mM PLP | 100 mM ThD | 4M NaCl | 50 mM EDTA | 1M MgCl2 | Enzyme | Water | Total |
|---|---|---|---|---|---|---|---|---|---|---|---|---|---|---|
| LysA | | | | 1.875 | | 1.25 | 0.05 | | | | 0.025 | 1 | 0.8 | 5 |
| KdcA | | | | 1.875 | | 1.25 | | 0.05 | | | 0.025 | 1 | 0.8 | 5 |
| KivD | | | | 1.875 | | 1.25 | | 0.05 | | | 0.025 | 1 | 0.8 | 5 |
| Kgd | | | | 1.875 | | 1.25 | | 0.05 | | | 0.025 | 1 | 0.8 | 5 |
| Lysin DC | | | | | 1.875 | 1.25 | 0.05 | | | | 0.025 | 1 | 0.8 | 5 |
| Ornithine DC LJ110 | | 1.875 | | | | 1.25 | 0.05 | | | | 0.025 | 1 | 0.8 | 5 |
| Ornithine DC DH5a | | 1.875 | | | | 1.25 | 0.05 | | | | 0.025 | 1 | 0.8 | 5 |
| Blanco | | | | | | 1.875 | 0.05 | | | | 0.025 | 1 | 2.05 | 5 |
| Blanco | | | | | | 1.875 | 1.25 | 0.05 | | | 0.025 | | 1.8 | 5 |

All N-Ac-Ornithine towards N-Ac-DAB reactions were stirred and incubated at 37° C. Samples were taken at 0; 2; 18; 28 and 44 hours and stored at −20° C. For analysis 500 μl of each sample was added to 500 μl of acetonitril and spinned at maximum speed for 10 minutes. Samples are analysed on TLC and run with an eluent of ammonia:methanol (1:1) and stained with a ninhydride spray. For quantitative analysis the samples are measured by LC-MS-MS according to the method described below.

HPLC-MS Analysis Method for the Determination of N-Acetyl-DAB

Sample Preparation:

A mixture of acetonitrile and water with 0.2% of formic acid is used to dilute the sample. The percentage of acetonitrile must be at least 50%

Experiments were performed on the PE SCIEX API2000 LC-MS/MS from Applied Biosystems.

LC Conditions:

| Column | 50 × 4.6 mm, HP HILIC, 3 μm (Alltech) |
|---|---|
| Column temperature | room temperature (24° C.) |
| Eluent | A: acetonitrile containing 0.2% formic acid |
| | B: water containing 0.2% formic acid |

| | time (min) | % eluent B |
|---|---|---|
| Gradient | 0 | 5 |
| | 2.5 | 20 |
| | 8 | 20 |
| | 8.1 | 5 |
| | 12 | 5 |
| Flow | 1 ml/min, before entering the MS the flow is split 1:5 | |
| Injection volume | 2 μl | |

MS Conditions:

| Ionisation | positive ion turbo ionspray | |
|---|---|---|
| | source conditions | ionspray voltage: 5 kV |
| | | temperature: 400° C. |
| | | defragmentation potential: 11 V |
| | | focusing potential: 350 V |
| Scan mode (N—Ac-DAB) | selective ion mode | m/z 72 & 114 (dwell time 200 msec) |

Under the applied conditions N—Ac-DAB elutes at 4.2 minutes

Results of Bioconversion of $N^5$-Acetyl-Ornithine Towards N-Acetyl-DAB

For the conversion of ornithine towards DAB the end time samples (44 hrs.) are analysed on TLC (FIG. 1).

All end time samples were analyzed with LC-MS-MS. Those showing a value of at least 3 micromol above the level of the control samples are shown in table 8.

TABLE 8

LC-MS-MS results of bioconversion N-Acetyl DAB

| | m/z 131 → 72 | m/z 131 → 114 |
|---|---|---|
| sample | micromol/l | micromol/l |
| 1 | 9 | — |
| 3 | 3 | — |
| 4 | 4 | 3 |
| 5 | 10 | 8 |
| 6 | 5 | 4 |
| | mmol/l | mmol/l |
| CB200109 | 370 | 344 |

The invention claimed is:

1. An in vitro method for the preparation of 1,4-diaminobutane [DAB] comprising
   a) enzymatically preparing N-acetyl DAB which comprises a step of contacting $N^5$-acetyl ornithine with a decarboxylase (EC 4.1.1), or a step of contacting N-acetyl-4-aminobutyraldehyde with an aminotransferase (EC 2.6.1) to produce an enzymatic reaction mixture
   (b) recovering the N-acetyl-DAB from the enzymatic reaction mixture, and
   (c) converting the recovered-N-acetyl-DAB into DAB in an in vitro process comprising at least one further step which is an enzymatic conversion comprising contacting N-acetyl DAB with a hydrolytic enzyme selected from the group consisting of carboxylic ester hydrolases (E.C. 3.1.1), thiolester hydrolases (E.C. 3.1.2) and peptidases (E.C 3.4), or a chemical conversion involving deacylation by $(PhO)_3PCl_2$ reagent.

2. The in vitro method according to claim 1, wherein in the recovery of the N-acetyl-DAB from the enzymatic reaction mixture is carried out by at least one step selected from the group consisting of filtration, sedimentation, crystallization, affinity chromatography, size exclusion chromatography, membrane separation and evaporation.

3. The in vitro method for the preparation of DAB according to claim 1, wherein the enzymatic conversion comprises contacting said N-acetyl-DAB with a hydrolytic enzyme.

4. The in vitro method according to claim 3, wherein the hydrolytic enzyme is a peptidase selected from the group of a serine carboxypeptidase, a metallocarboxypeptidase, a cysteine carboxypeptidase, a serine endopeptidase, a cysteine endopeptidase, an aspartic endopeptidase and a metalloendopeptidase.

5. The in vitro method according to claim 4, wherein the hydrolytic enzyme is a serine endopeptidase.

6. The in vitro method according to claim 5, wherein the serine endopeptidase is a subtilisin.

7. The in vitro method according to claim 5, wherein the serine endopeptidase is subtilisin Carlsberg.

* * * * *

SEQUENCE LISTING

<160> NUMBER OF SEQ ID NOS: 26

<210> SEQ ID NO 1
<211> LENGTH: 1371
<212> TYPE: DNA
<213> ORGANISM: Pseudomonas aeruginosa
<220> FEATURE:
<221> NAME/KEY: CDS
<222> LOCATION: (1)..(1371)
<223> OTHER INFORMATION: amino transferase gi9946143

<400> SEQUENCE: 1

| | | | | | | | | | | | | | | | | |
|---|---|---|---|---|---|---|---|---|---|---|---|---|---|---|---|---|
| atg | aac | agc | caa | atc | acc | aac | gcc | aag | acc | cgt | gag | tgg | cag | gcg | ttg | 48 |
| Met | Asn | Ser | Gln | Ile | Thr | Asn | Ala | Lys | Thr | Arg | Glu | Trp | Gln | Ala | Leu | |
| 1 | | | | 5 | | | | | 10 | | | | | 15 | | |
| agc | cgc | gac | cac | cat | ctg | ccg | ccg | ttc | acc | gac | tac | aag | cag | ttg | aac | 96 |
| Ser | Arg | Asp | His | His | Leu | Pro | Pro | Phe | Thr | Asp | Tyr | Lys | Gln | Leu | Asn | |
| | | | 20 | | | | | 25 | | | | | 30 | | | |
| gag | aag | ggc | gcg | cgg | atc | atc | acc | aag | gcc | gaa | ggc | gtc | tat | atc | tgg | 144 |
| Glu | Lys | Gly | Ala | Arg | Ile | Ile | Thr | Lys | Ala | Glu | Gly | Val | Tyr | Ile | Trp | |
| | | 35 | | | | | 40 | | | | | 45 | | | | |
| gac | agc | gag | ggc | aac | aag | atc | ctc | gat | gcg | atg | gcc | ggc | ctc | tgg | tgc | 192 |
| Asp | Ser | Glu | Gly | Asn | Lys | Ile | Leu | Asp | Ala | Met | Ala | Gly | Leu | Trp | Cys | |
| | 50 | | | | | 55 | | | | | 60 | | | | | |
| gtc | aac | gtc | ggc | tac | ggc | cgc | gag | gag | ctg | gtc | cag | gcc | gcc | acc | cgg | 240 |
| Val | Asn | Val | Gly | Tyr | Gly | Arg | Glu | Glu | Leu | Val | Gln | Ala | Ala | Thr | Arg | |
| 65 | | | | | 70 | | | | | 75 | | | | | 80 | |
| cag | atg | cgc | gag | ttg | ccg | ttc | tac | aac | ctg | ttc | ttc | cag | acc | gcc | cac | 288 |
| Gln | Met | Arg | Glu | Leu | Pro | Phe | Tyr | Asn | Leu | Phe | Phe | Gln | Thr | Ala | His | |
| | | | | 85 | | | | | 90 | | | | | 95 | | |
| ccg | ccg | gtg | gtc | gag | ctg | gcc | aag | gcg | atc | gcc | gac | gtc | gct | ccg | gaa | 336 |
| Pro | Pro | Val | Val | Glu | Leu | Ala | Lys | Ala | Ile | Ala | Asp | Val | Ala | Pro | Glu | |
| | | | 100 | | | | | 105 | | | | | 110 | | | |
| ggc | atg | aac | cac | gtg | ttc | ttc | acc | ggc | tcc | ggc | tcc | gag | gcc | aac | gac | 384 |
| Gly | Met | Asn | His | Val | Phe | Phe | Thr | Gly | Ser | Gly | Ser | Glu | Ala | Asn | Asp | |
| | | 115 | | | | | 120 | | | | | 125 | | | | |
| acc | gtg | ctg | cgt | atg | gtc | cgc | cac | tat | tgg | gcg | acc | aag | ggc | cag | ccg | 432 |
| Thr | Val | Leu | Arg | Met | Val | Arg | His | Tyr | Trp | Ala | Thr | Lys | Gly | Gln | Pro | |
| | 130 | | | | | 135 | | | | | 140 | | | | | |
| cag | aag | aaa | gtg | gtg | atc | ggc | cgc | tgg | aac | ggc | tac | cac | ggc | tcc | acc | 480 |
| Gln | Lys | Lys | Val | Val | Ile | Gly | Arg | Trp | Asn | Gly | Tyr | His | Gly | Ser | Thr | |
| 145 | | | | | 150 | | | | | 155 | | | | | 160 | |
| gtc | gcc | ggc | gtc | agc | ctg | ggc | ggc | atg | aag | gcg | ttg | cat | gag | cag | ggt | 528 |
| Val | Ala | Gly | Val | Ser | Leu | Gly | Gly | Met | Lys | Ala | Leu | His | Glu | Gln | Gly | |
| | | | | 165 | | | | | 170 | | | | | 175 | | |
| gat | ttc | ccc | atc | ccg | ggc | atc | gtc | cac | atc | gcc | cag | ccc | tac | tgg | tac | 576 |
| Asp | Phe | Pro | Ile | Pro | Gly | Ile | Val | His | Ile | Ala | Gln | Pro | Tyr | Trp | Tyr | |
| | | | 180 | | | | | 185 | | | | | 190 | | | |
| ggc | gag | ggc | ggc | gac | atg | tcg | ccg | gac | gag | ttc | ggc | gtc | tgg | gcc | gcc | 624 |
| Gly | Glu | Gly | Gly | Asp | Met | Ser | Pro | Asp | Glu | Phe | Gly | Val | Trp | Ala | Ala | |
| | | 195 | | | | | 200 | | | | | 205 | | | | |
| gag | cag | ttg | gag | aag | aag | att | ctc | gaa | gtg | ggc | gag | gaa | aac | gtc | gcc | 672 |
| Glu | Gln | Leu | Glu | Lys | Lys | Ile | Leu | Glu | Val | Gly | Glu | Glu | Asn | Val | Ala | |
| | 210 | | | | | 215 | | | | | 220 | | | | | |
| gcc | ttc | atc | gcc | gag | ccg | atc | cag | ggc | gcc | ggc | ggc | gtg | atc | gtc | ccg | 720 |
| Ala | Phe | Ile | Ala | Glu | Pro | Ile | Gln | Gly | Ala | Gly | Gly | Val | Ile | Val | Pro | |
| 225 | | | | | 230 | | | | | 235 | | | | | 240 | |
| ccg | gac | acc | tac | tgg | ccg | aag | atc | cgc | gag | atc | ctc | gcc | aag | tac | gac | 768 |
| Pro | Asp | Thr | Tyr | Trp | Pro | Lys | Ile | Arg | Glu | Ile | Leu | Ala | Lys | Tyr | Asp | |
| | | | | 245 | | | | | 250 | | | | | 255 | | |
| atc | ctg | ttc | atc | gcc | gac | gaa | gtg | atc | tgc | ggc | ttc | ggc | cgt | acc | ggc | 816 |
| Ile | Leu | Phe | Ile | Ala | Asp | Glu | Val | Ile | Cys | Gly | Phe | Gly | Arg | Thr | Gly | |
| | | | 260 | | | | | 265 | | | | | 270 | | | |
| gag | tgg | ttc | ggc | agc | cag | tac | tac | ggc | aac | gcc | ccg | gac | ctg | atg | ccg | 864 |
| Glu | Trp | Phe | Gly | Ser | Gln | Tyr | Tyr | Gly | Asn | Ala | Pro | Asp | Leu | Met | Pro | |
| | | 275 | | | | | 280 | | | | | 285 | | | | |

| | | |
|---|---|---|
| atc gcc aag ggc ctc acc tcc ggc tac atc ccc atg ggc ggg gtg gtg<br>Ile Ala Lys Gly Leu Thr Ser Gly Tyr Ile Pro Met Gly Gly Val Val<br>        290                            295                            300 | 912 |
| gtg cgc gac gag atc gtc gaa gtg ctc aac cag ggc ggc gag ttc tac<br>Val Arg Asp Glu Ile Val Glu Val Leu Asn Gln Gly Gly Glu Phe Tyr<br>305                          310                        315                      320 | 960 |
| cac ggc ttc acc tat tcc ggt cac ccg gtg gcg gcc gtg gcc ctg<br>His Gly Phe Thr Tyr Ser Gly His Pro Val Ala Ala Val Ala Leu<br>                      325                        330                      335 | 1008 |
| gag aac atc cgc atc ctg cgc gaa gag aag atc atc gag aag gtg aag<br>Glu Asn Ile Arg Ile Leu Arg Glu Glu Lys Ile Ile Glu Lys Val Lys<br>        340                        345                        350 | 1056 |
| gcg gaa acg gca ccg tat ttg cag aaa cgc tgg cag gag ctg gcc gac<br>Ala Glu Thr Ala Pro Tyr Leu Gln Lys Arg Trp Gln Glu Leu Ala Asp<br>355                        360                        365 | 1104 |
| cac ccg ttg gtg ggc gaa gcg cgc ggg gtc ggc atg gtc gcc gcc ctg<br>His Pro Leu Val Gly Glu Ala Arg Gly Val Gly Met Val Ala Ala Leu<br>    370                        375                      380 | 1152 |
| gag ctg gtc aag aac aag aag acc cgc gag cgt ttc acc gac aag ggc<br>Glu Leu Val Lys Asn Lys Lys Thr Arg Glu Arg Phe Thr Asp Lys Gly<br>385                        390                        395                      400 | 1200 |
| gtc ggg atg ctg tgc cgg gaa cat tgt ttc cgc aac ggt ttg atc atg<br>Val Gly Met Leu Cys Arg Glu His Cys Phe Arg Asn Gly Leu Ile Met<br>                    405                        410                      415 | 1248 |
| cgc gcg gtg ggc gac act atg att atc tcg ccg ccg ctg gtg atc gat<br>Arg Ala Val Gly Asp Thr Met Ile Ile Ser Pro Pro Leu Val Ile Asp<br>        420                        425                        430 | 1296 |
| ccg tcg cag atc gat gag ttg atc acc ctg gcg cgc aag tgc ctc gat<br>Pro Ser Gln Ile Asp Glu Leu Ile Thr Leu Ala Arg Lys Cys Leu Asp<br>            435                        440                        445 | 1344 |
| cag acc gcc gcc gcc gtc ctg gct tga<br>Gln Thr Ala Ala Ala Val Leu Ala<br>        450                        455 | 1371 |

```
<210> SEQ ID NO 2
<211> LENGTH: 456
<212> TYPE: PRT
<213> ORGANISM: Pseudomonas aeruginosa

<400> SEQUENCE: 2
```

Met Asn Ser Gln Ile Thr Asn Ala Lys Thr Arg Glu Trp Gln Ala Leu
1               5                   10                  15

Ser Arg Asp His His Leu Pro Pro Phe Thr Asp Tyr Lys Gln Leu Asn
            20                  25                  30

Glu Lys Gly Ala Arg Ile Ile Thr Lys Ala Glu Gly Val Tyr Ile Trp
        35                  40                  45

Asp Ser Glu Gly Asn Lys Ile Leu Asp Ala Met Ala Gly Leu Trp Cys
    50                  55                  60

Val Asn Val Gly Tyr Gly Arg Glu Glu Leu Val Gln Ala Ala Thr Arg
65                  70                  75                  80

Gln Met Arg Glu Leu Pro Phe Tyr Asn Leu Phe Gln Thr Ala His
                85                  90                  95

Pro Pro Val Val Glu Leu Ala Lys Ala Ile Ala Asp Val Ala Pro Glu
            100                 105                 110

Gly Met Asn His Val Phe Phe Thr Gly Ser Gly Ser Glu Ala Asn Asp
        115                 120                 125

Thr Val Leu Arg Met Val Arg His Tyr Trp Ala Thr Lys Gly Gln Pro
    130                 135                 140

```
Gln Lys Lys Val Val Ile Gly Arg Trp Asn Gly Tyr His Gly Ser Thr
145                 150                 155                 160

Val Ala Gly Val Ser Leu Gly Gly Met Lys Ala Leu His Glu Gln Gly
            165                 170                 175

Asp Phe Pro Ile Pro Gly Ile Val His Ile Ala Gln Pro Tyr Trp Tyr
        180                 185                 190

Gly Glu Gly Gly Asp Met Ser Pro Asp Glu Phe Gly Val Trp Ala Ala
    195                 200                 205

Glu Gln Leu Glu Lys Lys Ile Leu Glu Val Gly Glu Glu Asn Val Ala
210                 215                 220

Ala Phe Ile Ala Glu Pro Ile Gln Gly Ala Gly Gly Val Ile Val Pro
225                 230                 235                 240

Pro Asp Thr Tyr Trp Pro Lys Ile Arg Glu Ile Leu Ala Lys Tyr Asp
            245                 250                 255

Ile Leu Phe Ile Ala Asp Glu Val Ile Cys Gly Phe Gly Arg Thr Gly
        260                 265                 270

Glu Trp Phe Gly Ser Gln Tyr Tyr Gly Asn Ala Pro Asp Leu Met Pro
    275                 280                 285

Ile Ala Lys Gly Leu Thr Ser Gly Tyr Ile Pro Met Gly Gly Val Val
290                 295                 300

Val Arg Asp Glu Ile Val Glu Val Leu Asn Gln Gly Gly Glu Phe Tyr
305                 310                 315                 320

His Gly Phe Thr Tyr Ser Gly His Pro Val Ala Ala Val Ala Leu
            325                 330                 335

Glu Asn Ile Arg Ile Leu Arg Glu Glu Lys Ile Ile Glu Lys Val Lys
        340                 345                 350

Ala Glu Thr Ala Pro Tyr Leu Gln Lys Arg Trp Gln Glu Leu Ala Asp
    355                 360                 365

His Pro Leu Val Gly Glu Ala Arg Gly Val Gly Met Val Ala Ala Leu
370                 375                 380

Glu Leu Val Lys Asn Lys Lys Thr Arg Glu Arg Phe Thr Asp Lys Gly
385                 390                 395                 400

Val Gly Met Leu Cys Arg Glu His Cys Phe Arg Asn Gly Leu Ile Met
            405                 410                 415

Arg Ala Val Gly Asp Thr Met Ile Ile Ser Pro Pro Leu Val Ile Asp
        420                 425                 430

Pro Ser Gln Ile Asp Glu Leu Ile Thr Leu Ala Arg Lys Cys Leu Asp
    435                 440                 445

Gln Thr Ala Ala Ala Val Leu Ala
    450                 455

<210> SEQ ID NO 3
<211> LENGTH: 1407
<212> TYPE: DNA
<213> ORGANISM: Pseudomonas aeruginosa
<220> FEATURE:
<221> NAME/KEY: CDS
<222> LOCATION: (1)..(1407)
<223> OTHER INFORMATION: amino transferase gi9951072

<400> SEQUENCE: 3 atg aac gca aga ctg cac gcc acg tcc ccc ctc ggc gac gcc gac ctg    48
Met Asn Ala Arg Leu His Ala Thr Ser Pro Leu Gly Asp Ala Asp Leu
1               5                   10                  15 gtc cgt gcc gac cag gcc cac tac atg cac ggc tac cac gtg ttc gac    96
Val Arg Ala Asp Gln Ala His Tyr Met His Gly Tyr His Val Phe Asp
            20                  25                  30
```

| | | | | | | | | | | | | | | | |
|---|---|---|---|---|---|---|---|---|---|---|---|---|---|---|---|
| gac | cac | cgc | gtc | aac | ggc | tcg | ctg | aac | atc | gcc | gcc | ggc | gac | ggc | gcc | 144 |
| Asp | His | Arg | Val | Asn | Gly | Ser | Leu | Asn | Ile | Ala | Ala | Gly | Asp | Gly | Ala | |
| | | | 35 | | | | 40 | | | | 45 | | | | | |

| tat | atc | tac | gac | acc | gcc | ggc | aac | cgc | tac | ctc | gac | gcg | gtg | ggc | ggc | 192 |
| Tyr | Ile | Tyr | Asp | Thr | Ala | Gly | Asn | Arg | Tyr | Leu | Asp | Ala | Val | Gly | Gly | |
| 50 | | | | | 55 | | | | | 60 | | | | | | |

| atg | tgg | tgc | acc | aac | atc | ggc | ctg | ggg | cgc | gag | gaa | atg | gct | cgc | acc | 240 |
| Met | Trp | Cys | Thr | Asn | Ile | Gly | Leu | Gly | Arg | Glu | Glu | Met | Ala | Arg | Thr | |
| 65 | | | | | 70 | | | | | 75 | | | | | 80 | |

| gtg | gcc | gag | cag | acc | cgc | ctg | ctg | gcc | tat | tcc | aat | ccc | ttc | tgc | gac | 288 |
| Val | Ala | Glu | Gln | Thr | Arg | Leu | Leu | Ala | Tyr | Ser | Asn | Pro | Phe | Cys | Asp | |
| | | | | 85 | | | | | 90 | | | | | 95 | | |

| atg | gcc | aac | ccg | cgc | gcc | atc | gaa | ctc | tgc | cgc | aag | ctc | gcc | gag | ctg | 336 |
| Met | Ala | Asn | Pro | Arg | Ala | Ile | Glu | Leu | Cys | Arg | Lys | Leu | Ala | Glu | Leu | |
| | | | 100 | | | | | 105 | | | | | 110 | | | |

| gcc | ccc | ggc | gac | ctc | gac | cac | gtg | ttc | ctc | acc | acc | ggc | ggt | tcc | acc | 384 |
| Ala | Pro | Gly | Asp | Leu | Asp | His | Val | Phe | Leu | Thr | Thr | Gly | Gly | Ser | Thr | |
| | | | | 115 | | | | | 120 | | | | | 125 | | |

| gcc | gtg | gac | acc | gcg | atc | cgc | ctc | atg | cac | tac | tac | cag | aac | tgc | cgc | 432 |
| Ala | Val | Asp | Thr | Ala | Ile | Arg | Leu | Met | His | Tyr | Tyr | Gln | Asn | Cys | Arg | |
| | 130 | | | | | 135 | | | | | 140 | | | | | |

| ggc | aag | cgc | gcc | aag | aag | cac | gtc | atc | acg | cgg | atc | aac | gcc | tac | cac | 480 |
| Gly | Lys | Arg | Ala | Lys | Lys | His | Val | Ile | Thr | Arg | Ile | Asn | Ala | Tyr | His | |
| 145 | | | | | 150 | | | | | 155 | | | | | 160 | |

| ggc | tcg | acc | ttc | ctc | ggc | atg | tcg | ctg | ggc | ggc | aag | agc | gcc | gac | cgg | 528 |
| Gly | Ser | Thr | Phe | Leu | Gly | Met | Ser | Leu | Gly | Gly | Lys | Ser | Ala | Asp | Arg | |
| | | | | 165 | | | | | 170 | | | | | 175 | | |

| ccg | gcc | gag | ttc | gac | ttc | ctc | gac | gag | cgc | atc | cac | cac | ctc | gcc | tgt | 576 |
| Pro | Ala | Glu | Phe | Asp | Phe | Leu | Asp | Glu | Arg | Ile | His | His | Leu | Ala | Cys | |
| | | | | 180 | | | | | 185 | | | | | 190 | | |

| ccc | tat | tac | tac | cgc | gct | ccg | gaa | ggg | ctg | ggc | gaa | gcc | gag | ttc | ctc | 624 |
| Pro | Tyr | Tyr | Tyr | Arg | Ala | Pro | Glu | Gly | Leu | Gly | Glu | Ala | Glu | Phe | Leu | |
| | | 195 | | | | | 200 | | | | | 205 | | | | |

| gat | ggc | ctg | gtg | gac | gag | ttc | gaa | cgc | aag | atc | ctc | gaa | ctg | ggc | gcc | 672 |
| Asp | Gly | Leu | Val | Asp | Glu | Phe | Glu | Arg | Lys | Ile | Leu | Glu | Leu | Gly | Ala | |
| | | 210 | | | | | 215 | | | | | 220 | | | | |

| gac | cgg | gtg | ggg | gcg | ttc | atc | tcc | gag | ccg | gtg | ttc | ggc | tcc | ggc | ggc | 720 |
| Asp | Arg | Val | Gly | Ala | Phe | Ile | Ser | Glu | Pro | Val | Phe | Gly | Ser | Gly | Gly | |
| 225 | | | | | 230 | | | | | 235 | | | | | 240 | |

| gtg | atc | gtc | ccg | ccc | gcg | ggc | tac | cac | agg | cgg | atg | tgg | gag | ctg | tgc | 768 |
| Val | Ile | Val | Pro | Pro | Ala | Gly | Tyr | His | Arg | Arg | Met | Trp | Glu | Leu | Cys | |
| | | | | 245 | | | | | 250 | | | | | 255 | | |

| cag | cgc | tac | gac | gtg | ctg | tac | atc | tcc | gac | gaa | gtg | gtg | acc | tcc | ttc | 816 |
| Gln | Arg | Tyr | Asp | Val | Leu | Tyr | Ile | Ser | Asp | Glu | Val | Val | Thr | Ser | Phe | |
| | | | 260 | | | | | 265 | | | | | 270 | | | |

| ggc | cgc | ctc | ggc | cac | ttc | ttc | gcc | agc | cag | gcg | gtg | ttc | ggc | gta | cag | 864 |
| Gly | Arg | Leu | Gly | His | Phe | Phe | Ala | Ser | Gln | Ala | Val | Phe | Gly | Val | Gln | |
| | | 275 | | | | | 280 | | | | | 285 | | | | |

| ccg | gac | atc | atc | ctc | acc | gcc | aag | ggc | ctc | acc | tcc | ggc | tac | cag | ccg | 912 |
| Pro | Asp | Ile | Ile | Leu | Thr | Ala | Lys | Gly | Leu | Thr | Ser | Gly | Tyr | Gln | Pro | |
| | 290 | | | | | 295 | | | | | 300 | | | | | |

| ctg | ggc | gcg | tgc | atc | ttc | tcc | cgg | cgc | atc | tgg | gag | gtg | atc | gcc | gag | 960 |
| Leu | Gly | Ala | Cys | Ile | Phe | Ser | Arg | Arg | Ile | Trp | Glu | Val | Ile | Ala | Glu | |
| 305 | | | | | 310 | | | | | 315 | | | | | 320 | |

| ccg | gac | aag | ggc | cgc | tgc | ttc | agc | cat | ggt | ttc | acc | tac | tcc | ggc | cac | 1008 |
| Pro | Asp | Lys | Gly | Arg | Cys | Phe | Ser | His | Gly | Phe | Thr | Tyr | Ser | Gly | His | |
| | | | | 325 | | | | | 330 | | | | | 335 | | |

| ccg | gtg | gcc | tgc | gcg | gcg | gcg | ctg | aag | aac | atc | gag | atc | atc | gag | cgc | 1056 |
| Pro | Val | Ala | Cys | Ala | Ala | Ala | Leu | Lys | Asn | Ile | Glu | Ile | Ile | Glu | Arg | |

```
                    340             345             350
gag ggc ttg ctc gcc cac gcc gac gag gtc ggc cgc tac ttc gag gag       1104
Glu Gly Leu Leu Ala His Ala Asp Glu Val Gly Arg Tyr Phe Glu Glu
            355                 360                 365 cgc ctg caa agc ctc cgc gac ctg ccc atc gtc ggc gac gtg cgc ggg       1152
Arg Leu Gln Ser Leu Arg Asp Leu Pro Ile Val Gly Asp Val Arg Gly
    370                 375                 380 atg cgc ttc atg gcc tgt gtc gag ttc gtc gcc gac aag gcg agc aag       1200
Met Arg Phe Met Ala Cys Val Glu Phe Val Ala Asp Lys Ala Ser Lys
385                 390                 395                 400 gcg ctg ttt ccg gaa agc ctg aac atc ggc gag tgg gtc cac ctg cgg       1248
Ala Leu Phe Pro Glu Ser Leu Asn Ile Gly Glu Trp Val His Leu Arg
                405                 410                 415 gcg cag aag cgc ggc ctg ctg gtt cgt ccg atc gtc cac ctg aac gtg       1296
Ala Gln Lys Arg Gly Leu Leu Val Arg Pro Ile Val His Leu Asn Val
            420                 425                 430 atg tcg ccg ccg ctg atc ctc acc cgc gaa cag gtc gat acc gtg gtc       1344
Met Ser Pro Pro Leu Ile Leu Thr Arg Glu Gln Val Asp Thr Val Val
        435                 440                 445 cgg gtg ctg cgc gag agc atc gag gaa acc gtg gag gat ctt gtc cgc       1392
Arg Val Leu Arg Glu Ser Ile Glu Glu Thr Val Glu Asp Leu Val Arg
450                 455                 460 gcc ggt cac cgg taa                                                   1407
Ala Gly His Arg
465

<210> SEQ ID NO 4
<211> LENGTH: 468
<212> TYPE: PRT
<213> ORGANISM: Pseudomonas aeruginosa

<400> SEQUENCE: 4

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
```

-continued

```
            195                 200                 205
Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 5
<211> LENGTH: 1362
<212> TYPE: DNA
<213> ORGANISM: Vibrio fluvialis
<220> FEATURE:
<221> NAME/KEY: CDS
<222> LOCATION: (1)..(1362)
<223> OTHER INFORMATION: omega-aminotransferase JS17

<400> SEQUENCE: 5 atg aac aaa ccg caa agc tgg gaa gcc cgg gcc gag acc tat tcg ctc     48
Met Asn Lys Pro Gln Ser Trp Glu Ala Arg Ala Glu Thr Tyr Ser Leu
1               5                   10                  15 tat ggt ttc acc gac atg cct tcg ctg cat cag cgc ggc acg gtc gtc     96
Tyr Gly Phe Thr Asp Met Pro Ser Leu His Gln Arg Gly Thr Val Val
            20                  25                  30 gtg acc cat ggc gag gga ccc tat atc gtc gat gtg aat ggc cgg cgt    144
Val Thr His Gly Glu Gly Pro Tyr Ile Val Asp Val Asn Gly Arg Arg
        35                  40                  45 tat ctg gac gcc aac tcg ggc ctg tgg aac atg gtc gcg ggc ttt gac    192
Tyr Leu Asp Ala Asn Ser Gly Leu Trp Asn Met Val Ala Gly Phe Asp
```

```
            50                  55                  60
cac aag ggg ctg atc gac gcc gcc aag gcc caa tac gag cgt ttt ccc       240
His Lys Gly Leu Ile Asp Ala Ala Lys Ala Gln Tyr Glu Arg Phe Pro
 65                  70                  75                  80 ggt tat cac gcc ttt ttc ggc cgc atg tcc gat cag acg gta atg ctg       288
Gly Tyr His Ala Phe Phe Gly Arg Met Ser Asp Gln Thr Val Met Leu
                     85                  90                  95 tcg gaa aag ctg gtc gag gtg tcg ccc ttt gat tcg ggc cgg gtg ttc       336
Ser Glu Lys Leu Val Glu Val Ser Pro Phe Asp Ser Gly Arg Val Phe
                100                 105                 110 tat aca aac tcg ggg tcc gag gcg aat gac acc atg gtc aag atg cta       384
Tyr Thr Asn Ser Gly Ser Glu Ala Asn Asp Thr Met Val Lys Met Leu
                115                 120                 125 tgg ttc ctg cat gca gcc gag ggc aaa ccg caa aag cgc aag atc ctg       432
Trp Phe Leu His Ala Ala Glu Gly Lys Pro Gln Lys Arg Lys Ile Leu
    130                 135                 140 acc cgc tgg aac gcc tat cac ggc gtg acc gcc gtt tcg gcc agc atg       480
Thr Arg Trp Asn Ala Tyr His Gly Val Thr Ala Val Ser Ala Ser Met
145                 150                 155                 160 acc ggc aag ccc tat aat tcg gtc ttt ggc ctg ccg ctg ccg ggc ttt       528
Thr Gly Lys Pro Tyr Asn Ser Val Phe Gly Leu Pro Leu Pro Gly Phe
                    165                 170                 175 gtg cat ctg acc tgc ccg cat tac tgg cgc tat ggc gaa gag ggc gaa       576
Val His Leu Thr Cys Pro His Tyr Trp Arg Tyr Gly Glu Glu Gly Glu
                180                 185                 190 acc gaa gag cag ttc gtc gcc cgc ctc gcc cgc gag ctg gag gaa acg       624
Thr Glu Glu Gln Phe Val Ala Arg Leu Ala Arg Glu Leu Glu Glu Thr
                195                 200                 205 atc cag cgc gag ggc gcc gac acc atc gcc ggt ttc ttt gcc gaa ccg       672
Ile Gln Arg Glu Gly Ala Asp Thr Ile Ala Gly Phe Phe Ala Glu Pro
    210                 215                 220 gtg atg ggc gcg ggc ggc gtg att ccc ccg gcc aag ggc tat ttc cag       720
Val Met Gly Ala Gly Gly Val Ile Pro Pro Ala Lys Gly Tyr Phe Gln
225                 230                 235                 240 gcg atc ctg cca atc ctg cgc aaa tat gac atc ccg gtc atc tcg gac       768
Ala Ile Leu Pro Ile Leu Arg Lys Tyr Asp Ile Pro Val Ile Ser Asp
                    245                 250                 255 gag gtg atc tgc ggt ttc gga cgc acc ggt aac acc tgg ggc tgc gtg       816
Glu Val Ile Cys Gly Phe Gly Arg Thr Gly Asn Thr Trp Gly Cys Val
                260                 265                 270 acc tat gac ttt aca ccc gat gca atc atc tcg tcc aag aat ctt aca       864
Thr Tyr Asp Phe Thr Pro Asp Ala Ile Ile Ser Ser Lys Asn Leu Thr
                275                 280                 285 gcg ggc ttt ttc ccc atg ggg gcg gtg atc ctt ggc ccg gaa ctt tcc       912
Ala Gly Phe Phe Pro Met Gly Ala Val Ile Leu Gly Pro Glu Leu Ser
    290                 295                 300 aaa cgg ctg gaa acc gca atc gag gcg atc gag gaa ttc ccc cat ggc       960
Lys Arg Leu Glu Thr Ala Ile Glu Ala Ile Glu Glu Phe Pro His Gly
305                 310                 315                 320 ttt acc gcc tcg ggc cat ccg gtc ggc tgt gct att gcg ctg aaa gca       1008
Phe Thr Ala Ser Gly His Pro Val Gly Cys Ala Ile Ala Leu Lys Ala
                    325                 330                 335 atc gac gtg gtg atg aat gaa ggg ctg gct gag aac gtc cgc cgc ctt       1056
Ile Asp Val Val Met Asn Glu Gly Leu Ala Glu Asn Val Arg Arg Leu
                340                 345                 350 gcc ccc cgt ttc gag gaa agg ctg aaa cat atc gcc gag cgc ccg aac       1104
Ala Pro Arg Phe Glu Glu Arg Leu Lys His Ile Ala Glu Arg Pro Asn
                355                 360                 365 atc ggt gaa tat cgc ggc atc ggc ttc atg tgg gcg ctg gag gct gtc       1152
```

```
Ile Gly Glu Tyr Arg Gly Ile Gly Phe Met Trp Ala Leu Glu Ala Val
    370                 375                 380 aag gac aag gca agc aag acg ccg ttc gac ggc aac ctg tcg gtc agc     1200
Lys Asp Lys Ala Ser Lys Thr Pro Phe Asp Gly Asn Leu Ser Val Ser
385                 390                 395                 400 gag cgt atc gcc aat acc tgc acc gat ctg ggg ctg att tgc cgg ccg     1248
Glu Arg Ile Ala Asn Thr Cys Thr Asp Leu Gly Leu Ile Cys Arg Pro
                405                 410                 415 ctt ggt cag tcc gtc gtc ctt tgt ccg ccc ttt atc ctg acc gag gcg     1296
Leu Gly Gln Ser Val Val Leu Cys Pro Pro Phe Ile Leu Thr Glu Ala
            420                 425                 430 cag atg gat gag atg ttc gat aaa ctc gaa aaa gcc ctt gat aag gtc     1344
Gln Met Asp Glu Met Phe Asp Lys Leu Glu Lys Ala Leu Asp Lys Val
        435                 440                 445 ttt gcc gag gtt gcc tga                                             1362
Phe Ala Glu Val Ala
    450

<210> SEQ ID NO 6
<211> LENGTH: 453
<212> TYPE: PRT
<213> ORGANISM: Vibrio fluvialis

<400> SEQUENCE: 6

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255
```

```
Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
    275                 280                 285

Ala Gly Phe Phe Pro Met Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
                340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
                435                 440                 445

Phe Ala Glu Val Ala
    450

<210> SEQ ID NO 7
<211> LENGTH: 1362
<212> TYPE: DNA
<213> ORGANISM: Artificial
<220> FEATURE:
<223> OTHER INFORMATION: codon optimised sequence of
      omega-aminotransferase JS17

<400> SEQUENCE: 7
atgaacaagc cgcagtcctg ggaagcgcgt gctgaaactt actctctgta cggcttcact    60
gacatgccgt ctctgcacca gcgtggtact gttgttgtta ctcacggtga aggtccgtac   120
atcgttgacg ttaacggtcg tcgttacctg gatgctaact ccggtctgtg aacatggtt   180 gctggcttcg accacaaagg tctgatcgac gcagctaaag cgcagtacga acgtttccca   240
ggttaccacg cattcttcgg tcgtatgtct gaccagactg taatgctgtc tgagaagctg   300
gttgaagttt ctccgttcga ctccggtcgc gtattctaca ccaactccgg ttctgaagct   360
aacgacacca tggttaaaat gctgtggttc ctgcacgctg cagaaggtaa gccgcagaag   420
cgtaagatcc tgactcgctg gaacgcttac acggcgtaa ctgctgtttc tgcttctatg   480
accggtaagc cgtacaactc cgtattcggt ctgccgctgc cgggcttcgt tcacctgact   540
tgcccgcact actggcgtta cggtgaagaa ggtgaaactg aagagcagtt cgttgctcgt   600
ctggcacgtg aactggaaga aaccattcag cgtgaaggtg ctgacaccat cgctggcttc   660
ttcgctgaac cggtaatggg cgcaggtggt gttatcccgc agcaaaaagg ttacttccag   720
gctatcctgc cgattctgcg taaatacgac atcccggtta tctctgacga agttatctgc   780
ggtttcggtc gtactggtaa cacctggggc tgcgtaactt cgacttcac tccggatgct   840 atcatctctt ccaaaaacct gactgcaggc ttcttcccga tgggtgctgt tatcctgggt   900
```

```
ccggaactgt ctaaacgtct ggaaactgct atcgaagcaa tcgaagagtt cccgcacggc    960
ttcactgctt ctggtcaccc ggttggttgc gcaatcgcgc tgaaagcaat cgacgttgta   1020
atgaacgaag tctggcaga aaacgttcgt cgtctggcac cgcgcttcga agagcgtctg    1080
aaacacatcg ctgaacgtcc gaacatcggt gaataccgcg tatcggctt catgtgggcg    1140 ctggaagcgg ttaaagacaa agcgtctaaa actccgttcg acggtaacct gtctgtttct   1200
gaacgtatcg ctaacacctg tactgacctg ggtctgatct gccgtccgct gggtcagtct   1260
gttgttctgt gcccgccgtt catcctgact gaagcgcaga tggacgaaat gttcgacaaa   1320
ctggaaaaag cgctggataa agttttcgct gaagttgcgt aa                     1362
```

<210> SEQ ID NO 8
<211> LENGTH: 1644
<212> TYPE: DNA
<213> ORGANISM: Lactococcus lactis
<220> FEATURE:
<221> NAME/KEY: CDS
<222> LOCATION: (1)..(1644)
<223> OTHER INFORMATION: decarboxylase KdcA

<400> SEQUENCE: 8

```
atg tat aca gta gga gat tac ctg tta gac cga tta cac gag ttg gga     48
Met Tyr Thr Val Gly Asp Tyr Leu Leu Asp Arg Leu His Glu Leu Gly
1               5                   10                  15 att gaa gaa att ttt gga gtt cct ggt gac tat aac tta caa ttt tta     96
Ile Glu Glu Ile Phe Gly Val Pro Gly Asp Tyr Asn Leu Gln Phe Leu
            20                  25                  30 gat caa att att tca cgc gaa gat atg aaa tgg att gga aat gct aat    144
Asp Gln Ile Ile Ser Arg Glu Asp Met Lys Trp Ile Gly Asn Ala Asn
        35                  40                  45 gaa tta aat gct tct tat atg gct gat ggt tat gct cgt act aaa aaa    192
Glu Leu Asn Ala Ser Tyr Met Ala Asp Gly Tyr Ala Arg Thr Lys Lys
    50                  55                  60 gct gcc gca ttt ctc acc aca ttt gga gtc ggc gaa ttg agt gcg atc    240
Ala Ala Ala Phe Leu Thr Thr Phe Gly Val Gly Glu Leu Ser Ala Ile
65                  70                  75                  80 aat gga ctg gca gga agt tat gcc gaa aat tta cca gta gta gaa att    288
Asn Gly Leu Ala Gly Ser Tyr Ala Glu Asn Leu Pro Val Val Glu Ile
                85                  90                  95 gtt ggt tca cca act tca aaa gta caa aat gac gga aaa ttt gtc cat    336
Val Gly Ser Pro Thr Ser Lys Val Gln Asn Asp Gly Lys Phe Val His
            100                 105                 110 cat aca cta gca gat ggt gat ttt aaa cac ttt atg aag atg cat gaa    384
His Thr Leu Ala Asp Gly Asp Phe Lys His Phe Met Lys Met His Glu
        115                 120                 125 cct gtt aca gca gcg cgg act tta ctg aca gca gaa aat gcc aca tat    432
Pro Val Thr Ala Ala Arg Thr Leu Leu Thr Ala Glu Asn Ala Thr Tyr
    130                 135                 140 gaa att gac cga gta ctt tct caa tta cta aaa gaa aga aaa cca gtc    480
Glu Ile Asp Arg Val Leu Ser Gln Leu Leu Lys Glu Arg Lys Pro Val
145                 150                 155                 160 tat att aac tta cca gtc gat gtt gct gca gca aaa gca gag aag cct    528
Tyr Ile Asn Leu Pro Val Asp Val Ala Ala Ala Lys Ala Glu Lys Pro
                165                 170                 175 gca tta tct tta gaa aaa gaa agc tct aca aca aat aca act gaa caa    576
Ala Leu Ser Leu Glu Lys Glu Ser Ser Thr Thr Asn Thr Thr Glu Gln
            180                 185                 190 gtg att ttg agt aag att gaa gaa agt ttg aaa aat gcc caa aaa cca    624
Val Ile Leu Ser Lys Ile Glu Glu Ser Leu Lys Asn Ala Gln Lys Pro
```

|  |  |  |  |  |  |  |  |  |  |  |  |  |  |  |  |  |
|---|---|---|---|---|---|---|---|---|---|---|---|---|---|---|---|---|
|  |  |  | 195 |  |  |  | 200 |  |  |  | 205 |  |  |  |  |  |
| gta | gtg | att | gca | gga | cac | gaa | gta | att | agt | ttt | ggt | tta | gaa | aaa | acg | 672 |
| Val | Val | Ile | Ala | Gly | His | Glu | Val | Ile | Ser | Phe | Gly | Leu | Glu | Lys | Thr |  |
|  |  | 210 |  |  |  |  | 215 |  |  |  |  | 220 |  |  |  |  |
| gta | act | cag | ttt | gtt | tca | gaa | aca | aaa | cta | ccg | att | acg | aca | cta | aat | 720 |
| Val | Thr | Gln | Phe | Val | Ser | Glu | Thr | Lys | Leu | Pro | Ile | Thr | Thr | Leu | Asn |  |
| 225 |  |  |  |  | 230 |  |  |  |  | 235 |  |  |  |  | 240 |  |
| ttt | ggt | aaa | agt | gct | gtt | gat | gaa | tct | ttg | ccc | tca | ttt | tta | gga | ata | 768 |
| Phe | Gly | Lys | Ser | Ala | Val | Asp | Glu | Ser | Leu | Pro | Ser | Phe | Leu | Gly | Ile |  |
|  |  |  |  | 245 |  |  |  |  | 250 |  |  |  |  | 255 |  |  |
| tat | aac | ggg | aaa | ctt | tca | gaa | atc | agt | ctt | aaa | aat | ttt | gtg | gag | tcc | 816 |
| Tyr | Asn | Gly | Lys | Leu | Ser | Glu | Ile | Ser | Leu | Lys | Asn | Phe | Val | Glu | Ser |  |
|  |  |  | 260 |  |  |  |  | 265 |  |  |  |  | 270 |  |  |  |
| gca | gac | ttt | atc | cta | atg | ctt | gga | gtg | aag | ctt | acg | gac | tcc | tca | aca | 864 |
| Ala | Asp | Phe | Ile | Leu | Met | Leu | Gly | Val | Lys | Leu | Thr | Asp | Ser | Ser | Thr |  |
|  |  | 275 |  |  |  |  | 280 |  |  |  |  | 285 |  |  |  |  |
| ggt | gca | ttc | aca | cat | cat | tta | gat | gaa | aat | aaa | atg | att | tca | cta | aac | 912 |
| Gly | Ala | Phe | Thr | His | His | Leu | Asp | Glu | Asn | Lys | Met | Ile | Ser | Leu | Asn |  |
| 290 |  |  |  |  | 295 |  |  |  |  | 300 |  |  |  |  |  |  |
| ata | gat | gaa | gga | ata | att | ttc | aat | aaa | gtg | gta | gaa | gat | ttt | gat | ttt | 960 |
| Ile | Asp | Glu | Gly | Ile | Ile | Phe | Asn | Lys | Val | Val | Glu | Asp | Phe | Asp | Phe |  |
| 305 |  |  |  |  | 310 |  |  |  |  | 315 |  |  |  |  | 320 |  |
| aga | gca | gtg | gtt | tct | tct | tta | tca | gaa | tta | aaa | gga | ata | gaa | tat | gaa | 1008 |
| Arg | Ala | Val | Val | Ser | Ser | Leu | Ser | Glu | Leu | Lys | Gly | Ile | Glu | Tyr | Glu |  |
|  |  |  |  | 325 |  |  |  |  | 330 |  |  |  |  | 335 |  |  |
| gga | caa | tat | att | gat | aag | caa | tat | gaa | gaa | ttt | att | cca | tca | agt | gct | 1056 |
| Gly | Gln | Tyr | Ile | Asp | Lys | Gln | Tyr | Glu | Glu | Phe | Ile | Pro | Ser | Ser | Ala |  |
|  |  |  | 340 |  |  |  |  | 345 |  |  |  |  | 350 |  |  |  |
| ccc | tta | tca | caa | gac | cgt | cta | tgg | cag | gca | gtt | gaa | agt | ttg | act | caa | 1104 |
| Pro | Leu | Ser | Gln | Asp | Arg | Leu | Trp | Gln | Ala | Val | Glu | Ser | Leu | Thr | Gln |  |
|  |  | 355 |  |  |  |  | 360 |  |  |  |  | 365 |  |  |  |  |
| agc | aat | gaa | aca | atc | gtt | gct | gaa | caa | gga | acc | tca | ttt | ttt | gga | gct | 1152 |
| Ser | Asn | Glu | Thr | Ile | Val | Ala | Glu | Gln | Gly | Thr | Ser | Phe | Phe | Gly | Ala |  |
|  | 370 |  |  |  |  | 375 |  |  |  |  | 380 |  |  |  |  |  |
| tca | aca | att | ttc | tta | aaa | tca | aat | agt | cgt | ttt | att | gga | caa | cct | tta | 1200 |
| Ser | Thr | Ile | Phe | Leu | Lys | Ser | Asn | Ser | Arg | Phe | Ile | Gly | Gln | Pro | Leu |  |
| 385 |  |  |  |  | 390 |  |  |  |  | 395 |  |  |  |  | 400 |  |
| tgg | ggt | tct | att | gga | tat | act | ttt | cca | gcg | gct | tta | gga | agc | caa | att | 1248 |
| Trp | Gly | Ser | Ile | Gly | Tyr | Thr | Phe | Pro | Ala | Ala | Leu | Gly | Ser | Gln | Ile |  |
|  |  |  |  | 405 |  |  |  |  | 410 |  |  |  |  | 415 |  |  |
| gcg | gat | aaa | gag | agc | aga | cac | ctt | tta | ttt | att | ggt | gat | ggt | tca | ctt | 1296 |
| Ala | Asp | Lys | Glu | Ser | Arg | His | Leu | Leu | Phe | Ile | Gly | Asp | Gly | Ser | Leu |  |
|  |  |  | 420 |  |  |  |  | 425 |  |  |  |  | 430 |  |  |  |
| caa | ctt | acc | gta | caa | gaa | tta | gga | cta | tca | atc | aga | gaa | aaa | ctc | aat | 1344 |
| Gln | Leu | Thr | Val | Gln | Glu | Leu | Gly | Leu | Ser | Ile | Arg | Glu | Lys | Leu | Asn |  |
|  |  | 435 |  |  |  |  | 440 |  |  |  |  | 445 |  |  |  |  |
| cca | att | tgt | ttt | atc | ata | aat | aat | gat | ggt | tat | aca | gtt | gaa | aga | gaa | 1392 |
| Pro | Ile | Cys | Phe | Ile | Ile | Asn | Asn | Asp | Gly | Tyr | Thr | Val | Glu | Arg | Glu |  |
|  | 450 |  |  |  |  | 455 |  |  |  |  | 460 |  |  |  |  |  |
| atc | cac | gga | cct | act | caa | agt | tat | aac | gac | att | cca | atg | tgg | aat | tac | 1440 |
| Ile | His | Gly | Pro | Thr | Gln | Ser | Tyr | Asn | Asp | Ile | Pro | Met | Trp | Asn | Tyr |  |
| 465 |  |  |  |  | 470 |  |  |  |  | 475 |  |  |  |  | 480 |  |
| tcg | aaa | tta | cca | gaa | aca | ttt | gga | gca | aca | gaa | gat | cgt | gta | gta | tca | 1488 |
| Ser | Lys | Leu | Pro | Glu | Thr | Phe | Gly | Ala | Thr | Glu | Asp | Arg | Val | Val | Ser |  |
|  |  |  |  | 485 |  |  |  |  | 490 |  |  |  |  | 495 |  |  |
| aaa | att | gtt | aga | aca | gag | aat | gaa | ttt | gtg | tct | gtc | atg | aaa | gaa | gcc | 1536 |
| Lys | Ile | Val | Arg | Thr | Glu | Asn | Glu | Phe | Val | Ser | Val | Met | Lys | Glu | Ala |  |
|  |  |  | 500 |  |  |  |  | 505 |  |  |  |  | 510 |  |  |  |
| caa | gca | gat | gtc | aat | aga | atg | tat | tgg | ata | gaa | cta | gtt | ttg | gaa | aaa | 1584 |

```
Gln Ala Asp Val Asn Arg Met Tyr Trp Ile Glu Leu Val Leu Glu Lys
            515                 520                 525 gaa gat gcg cca aaa tta ctg aaa aaa atg ggt aaa tta ttt gct gag      1632
Glu Asp Ala Pro Lys Leu Leu Lys Lys Met Gly Lys Leu Phe Ala Glu
    530                 535                 540 caa aat aaa tag                                                      1644
Gln Asn Lys
545

<210> SEQ ID NO 9
<211> LENGTH: 547
<212> TYPE: PRT
<213> ORGANISM: Lactococcus lactis

<400> SEQUENCE: 9

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320
```

-continued

```
Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 10
<211> LENGTH: 1647
<212> TYPE: DNA
<213> ORGANISM: Lactococcus lactis
<220> FEATURE:
<221> NAME/KEY: CDS
<222> LOCATION: (1)..(1647)
<223> OTHER INFORMATION: decarboxylase KivD

<400> SEQUENCE: 10 atg tat aca gta gga gat tac cta tta gac cga tta cac gag tta gga      48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
            20                  25                  30 gat caa att att tcc cac aag gat atg aaa tgg gtc gga aat gct aat     144
Asp Gln Ile Ile Ser His Lys Asp Met Lys Trp Val Gly Asn Ala Asn
        35                  40                  45 gaa tta aat gct tca tat atg gct gat ggc tat gct cgt act aaa aaa     192
Glu Leu Asn Ala Ser Tyr Met Ala Asp Gly Tyr Ala Arg Thr Lys Lys
    50                  55                  60 gct gcc gca ttt ctt aca acc ttt gga gta ggt gaa ttg agt gca gtt     240
Ala Ala Ala Phe Leu Thr Thr Phe Gly Val Gly Glu Leu Ser Ala Val
65                  70                  75                  80 aat gga tta gca gga agt tac gcc gaa aat tta cca gta gta gaa ata     288
Asn Gly Leu Ala Gly Ser Tyr Ala Glu Asn Leu Pro Val Val Glu Ile
```

```
                    85                   90                     95
gtg gga tca cct aca tca aaa gtt caa aat gaa gga aaa ttt gtt cat      336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa      384
His Thr Leu Ala Asp Gly Asp Phe Lys His Phe Met Lys Met His Glu
        115                 120                 125 cct gtt aca gca gct cga act tta ctg aca gca gaa aat gca acc gtt      432
Pro Val Thr Ala Ala Arg Thr Leu Leu Thr Ala Glu Asn Ala Thr Val
130                 135                 140 gaa att gac cga gta ctt tct gca cta tta aaa gaa aga aaa cct gtc      480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc      528
Tyr Ile Asn Leu Pro Val Asp Val Ala Ala Ala Lys Ala Glu Lys Pro
                165                 170                 175 tca ctc cct ttg aaa aag gaa aac tca act tca aat aca agt gac caa      576
Ser Leu Pro Leu Lys Lys Glu Asn Ser Thr Ser Asn Thr Ser Asp Gln
            180                 185                 190 gaa att ttg aac aaa att caa gaa agc ttg aaa aat gcc aaa aaa cca      624
Glu Ile Leu Asn Lys Ile Gln Glu Ser Leu Lys Asn Ala Lys Lys Pro
        195                 200                 205 atc gtg att aca gga cat gaa ata att agt ttt ggc tta gaa aaa aca      672
Ile Val Ile Thr Gly His Glu Ile Ile Ser Phe Gly Leu Glu Lys Thr
210                 215                 220 gtc act caa ttt att tca aag aca aaa cta cct att acg aca tta aac      720
Val Thr Gln Phe Ile Ser Lys Thr Lys Leu Pro Ile Thr Thr Leu Asn
225                 230                 235                 240 ttt ggt aaa agt tca gtt gat gaa gcc ctc cct tca ttt tta gga atc      768
Phe Gly Lys Ser Ser Val Asp Glu Ala Leu Pro Ser Phe Leu Gly Ile
                245                 250                 255 tat aat ggt aca ctc tca gag cct aat ctt aaa gaa ttc gtg gaa tca      816
Tyr Asn Gly Thr Leu Ser Glu Pro Asn Leu Lys Glu Phe Val Glu Ser
            260                 265                 270 gcc gac ttc atc ttg atg ctt gga gtt aaa ctc aca gac tct tca aca      864
Ala Asp Phe Ile Leu Met Leu Gly Val Lys Leu Thr Asp Ser Ser Thr
        275                 280                 285 gga gcc ttc act cat cat tta aat gaa aat aaa atg att tca ctg aat      912
Gly Ala Phe Thr His His Leu Asn Glu Asn Lys Met Ile Ser Leu Asn
290                 295                 300 ata gat gaa gga aaa ata ttt aac gaa aga atc caa aat ttt gat ttt      960
Ile Asp Glu Gly Lys Ile Phe Asn Glu Arg Ile Gln Asn Phe Asp Phe
305                 310                 315                 320 gaa tcc ctc atc tcc tct ctc tta gac cta agc gaa ata gaa tac aaa     1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg     1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa     1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct     1152
Ser Asn Glu Thr Ile Val Ala Glu Gln Gly Thr Ser Phe Phe Gly Ala
370                 375                 380 tca tca att ttc tta aaa tca aag agt cat ttt att ggt caa ccc tta     1200
Ser Ser Ile Phe Leu Lys Ser Lys Ser His Phe Ile Gly Gln Pro Leu
385                 390                 395                 400 tgg gga tca att gga tat aca ttc cca gca gca tta gga agc caa att     1248
```

```
                                        -continued

Trp Gly Ser Ile Gly Tyr Thr Phe Pro Ala Leu Gly Ser Gln Ile
            405                 410                 415 gca gat aaa gaa agc aga cac ctt tta ttt att ggt gat ggt tca ctt    1296
Ala Asp Lys Glu Ser Arg His Leu Leu Phe Ile Gly Asp Gly Ser Leu
            420                 425                 430 caa ctt aca gtg caa gaa tta gga tta gca atc aga gaa aaa att aat    1344
Gln Leu Thr Val Gln Glu Leu Gly Leu Ala Ile Arg Glu Lys Ile Asn
            435                 440                 445 cca att tgc ttt att atc aat aat gat ggt tat aca gtc gaa aga gaa    1392
Pro Ile Cys Phe Ile Ile Asn Asn Asp Gly Tyr Thr Val Glu Arg Glu
        450                 455                 460 att cat gga cca aat caa agc tac aat gat att cca atg tgg aat tac    1440
Ile His Gly Pro Asn Gln Ser Tyr Asn Asp Ile Pro Met Trp Asn Tyr
465                 470                 475                 480 tca aaa tta cca gaa tcg ttt gga gca aca gaa gat cga gta gtc tca    1488
Ser Lys Leu Pro Glu Ser Phe Gly Ala Thr Glu Asp Arg Val Val Ser
                485                 490                 495 aaa atc gtt aga act gaa aat gaa ttt gtg tct gtc atg aaa gaa gct    1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa    1584
Gln Ala Asp Pro Asn Arg Met Tyr Trp Ile Glu Leu Ile Leu Ala Lys
        515                 520                 525 gaa ggt gca cca aaa gta ctg aaa aaa atg ggc aaa cta ttt gct gaa    1632
Glu Gly Ala Pro Lys Val Leu Lys Lys Met Gly Lys Leu Phe Ala Glu
530                 535                 540 caa aat aaa tca taa                                                 1647
Gln Asn Lys Ser
545

<210> SEQ ID NO 11
<211> LENGTH: 548
<212> TYPE: PRT
<213> ORGANISM: Lactococcus lactis

<400> SEQUENCE: 11

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175
```

```
Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 12
<211> LENGTH: 1263
<212> TYPE: DNA
<213> ORGANISM: Escherichia coli
<220> FEATURE:
```

<221> NAME/KEY: CDS
<222> LOCATION: (1)..(1263)
<223> OTHER INFORMATION: decarboxylase LysA

<400> SEQUENCE: 12

| | | |
|---|---|---|
| atg cca cat tca ctg ttc agc acc gat acc gat ctc acc gcc gaa aat<br>Met Pro His Ser Leu Phe Ser Thr Asp Thr Asp Leu Thr Ala Glu Asn<br>1                   5                   10               15 | | 48 |
| ctg ctg cgt ttg ccc gct gaa ttt ggc tgc ccg gtg tgg gtc tac gat<br>Leu Leu Arg Leu Pro Ala Glu Phe Gly Cys Pro Val Trp Val Tyr Asp<br>            20                   25               30 | | 96 |
| gcg caa att att cgt cgg cag att gca gcg ctg aaa cag ttt gat gtg<br>Ala Gln Ile Ile Arg Arg Gln Ile Ala Ala Leu Lys Gln Phe Asp Val<br>                35                  40               45 | | 144 |
| gtg cgc ttt gca cag aaa gcc tgt tcc aat att cat att ttg cgc tta<br>Val Arg Phe Ala Gln Lys Ala Cys Ser Asn Ile His Ile Leu Arg Leu<br>50                  55                  60 | | 192 |
| atg cgt gag cag ggc gtg aaa gtg gat tcc gtc tcg tta ggc gaa ata<br>Met Arg Glu Gln Gly Val Lys Val Asp Ser Val Ser Leu Gly Glu Ile<br>65                    70                  75              80 | | 240 |
| gag cgt gcg ttg gcg gcg ggt tac aat ccg caa acg cac ccc gat gat<br>Glu Arg Ala Leu Ala Ala Gly Tyr Asn Pro Gln Thr His Pro Asp Asp<br>                  85                   90               95 | | 288 |
| att gtt ttt acg gca gat gtt atc gat cag gcg acg ctt gaa cgc gtc<br>Ile Val Phe Thr Ala Asp Val Ile Asp Gln Ala Thr Leu Glu Arg Val<br>                      100                 105             110 | | 336 |
| agt gaa ttg caa att ccg gtg aat gcg ggt tct gtt gat atg ctc gac<br>Ser Glu Leu Gln Ile Pro Val Asn Ala Gly Ser Val Asp Met Leu Asp<br>               115                 120             125 | | 384 |
| caa ctg ggc cag gtt tcg cca ggg cat cgg gta tgg ctg cgc gtt aat<br>Gln Leu Gly Gln Val Ser Pro Gly His Arg Val Trp Leu Arg Val Asn<br>          130                 135             140 | | 432 |
| ccg ggg ttt ggt cac gga cat agc caa aaa acc aat acc ggt ggc gaa<br>Pro Gly Phe Gly His Gly His Ser Gln Lys Thr Asn Thr Gly Gly Glu<br>145                  150                 155              160 | | 480 |
| aac agc aag cac ggt atc tgg tac acc gat ctg ccc gcc gca ctg gac<br>Asn Ser Lys His Gly Ile Trp Tyr Thr Asp Leu Pro Ala Ala Leu Asp<br>                      165                 170             175 | | 528 |
| gtg ata caa cgt cat cat ctg cag ctg gtc ggc att cac atg cac att<br>Val Ile Gln Arg His His Leu Gln Leu Val Gly Ile His Met His Ile<br>               180                 185             190 | | 576 |
| ggt tct ggc gtt gat tat gcc cat ctg gaa cag gtg tgt ggt gct atg<br>Gly Ser Gly Val Asp Tyr Ala His Leu Glu Gln Val Cys Gly Ala Met<br>          195                 200             205 | | 624 |
| gtg cgt cag gtc atc gaa ttc ggt cag gat tta cag gct att tct gcg<br>Val Arg Gln Val Ile Glu Phe Gly Gln Asp Leu Gln Ala Ile Ser Ala<br>          210                 215             220 | | 672 |
| ggc ggt ggg ctt tct gtt cct tat caa cag ggt gaa gag gcg gtt gat<br>Gly Gly Gly Leu Ser Val Pro Tyr Gln Gln Gly Glu Glu Ala Val Asp<br>225                  230                 235             240 | | 720 |
| acc gaa cat tat tat ggt ctg tgg aat gcc gcg cgt gag caa atc gcc<br>Thr Glu His Tyr Tyr Gly Leu Trp Asn Ala Ala Arg Glu Gln Ile Ala<br>                      245                 250             255 | | 768 |
| cgc cat ttg ggc cac cct gtg aaa ctg gaa att gaa ccg ggt cgc ttc<br>Arg His Leu Gly His Pro Val Lys Leu Glu Ile Glu Pro Gly Arg Phe<br>          260                 265             270 | | 816 |
| ctg gta gcg cag tct ggc gta tta att act cag gtg cgg agc gtc aaa<br>Leu Val Ala Gln Ser Gly Val Leu Ile Thr Gln Val Arg Ser Val Lys<br>          275                 280             285 | | 864 |
| caa atg ggg agc cgc cac ttt gtg ctg gtt gat gcc ggg ttc aac gat | | 912 |

```
Gln Met Gly Ser Arg His Phe Val Leu Val Asp Ala Gly Phe Asn Asp
    290             295                 300 ctg atg cgc ccg gca atg tac ggt agt tac cac cat atc agt gcc ctg      960
Leu Met Arg Pro Ala Met Tyr Gly Ser Tyr His His Ile Ser Ala Leu
305             310                 315                 320 gca gct gat ggt cgt tct ctg gaa cac gcg cca acg gtg gaa acc gtc     1008
Ala Ala Asp Gly Arg Ser Leu Glu His Ala Pro Thr Val Glu Thr Val
                325                 330                 335 gtc gcc gga ccg tta tgt gaa tcg ggc gat gtc ttt acc cag cag gaa     1056
Val Ala Gly Pro Leu Cys Glu Ser Gly Asp Val Phe Thr Gln Gln Glu
            340                 345                 350 ggg gga aat gtt gaa acc cgc gcc ttg ccg gaa gtg aag gca ggt gat     1104
Gly Gly Asn Val Glu Thr Arg Ala Leu Pro Glu Val Lys Ala Gly Asp
        355                 360                 365 tat ctg gta ctg cat gat aca ggg gca tat ggc gca tca atg tca tcc     1152
Tyr Leu Val Leu His Asp Thr Gly Ala Tyr Gly Ala Ser Met Ser Ser
370                 375                 380 aac tac aat agc cgt ccg ctg tta cca gaa gtt ctg ttt gat aat ggt     1200
Asn Tyr Asn Ser Arg Pro Leu Leu Pro Glu Val Leu Phe Asp Asn Gly
385                 390                 395                 400 cag gcg cgg ttg att cgc cgt cgc cag acc atc gaa gaa tta ctg gcg     1248
Gln Ala Arg Leu Ile Arg Arg Arg Gln Thr Ile Glu Glu Leu Leu Ala
                405                 410                 415 ctg gaa ttg ctt taa                                                  1263
Leu Glu Leu Leu
            420

<210> SEQ ID NO 13
<211> LENGTH: 420
<212> TYPE: PRT
<213> ORGANISM: Escherichia coli

<400> SEQUENCE: 13

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190
```

```
Gly Ser Gly Val Asp Tyr Ala His Leu Glu Gln Val Cys Gly Ala Met
            195                 200                 205

Val Arg Gln Val Ile Glu Phe Gly Gln Asp Leu Gln Ala Ile Ser Ala
        210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 14
<211> LENGTH: 1362
<212> TYPE: DNA
<213> ORGANISM: Paracoccus denitrificans
<220> FEATURE:
<221> NAME/KEY: CDS
<222> LOCATION: (1)..(1362)
<223> OTHER INFORMATION: aminotransferase zp00628577

<400> SEQUENCE: 14 atg aac caa ccg caa agc tgg gaa gcc cgg gcc gag acc tat tcg ctc     48
Met Asn Gln Pro Gln Ser Trp Glu Ala Arg Ala Glu Thr Tyr Ser Leu
1               5                   10                  15 tac ggt ttc acc gac atg ccc tcg gtc cat cag cgg ggc acg gtc gtc     96
Tyr Gly Phe Thr Asp Met Pro Ser Val His Gln Arg Gly Thr Val Val
            20                  25                  30 gtg acc cat ggc gag ggg ccc tat atc gtc gat gtc cat ggc cgc cgc    144
Val Thr His Gly Glu Gly Pro Tyr Ile Val Asp Val His Gly Arg Arg
        35                  40                  45 tat ctg gat gcc aat tcg ggc ctg tgg aac atg gtc gcg ggc ttc gac    192
Tyr Leu Asp Ala Asn Ser Gly Leu Trp Asn Met Val Ala Gly Phe Asp
    50                  55                  60 cac aag ggc ctg atc gag gcc gcc aag gcg caa tac gac cgc ttt ccc    240
His Lys Gly Leu Ile Glu Ala Ala Lys Ala Gln Tyr Asp Arg Phe Pro
65                  70                  75                  80 ggc tat cac gcc ttt ttc ggc cgc atg tcc gac cag acc gtg atg ctg    288
Gly Tyr His Ala Phe Phe Gly Arg Met Ser Asp Gln Thr Val Met Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 85  |     |     |     |     | 90  |     |     |     |     | 95  |     |     |      |
| tcg | gaa | aag | ctg | gtc | gag | gtc | tcg | cca | ttc | gac | aac | ggc | cgg | gtc | ttc | 336  |
| Ser | Glu | Lys | Leu | Val | Glu | Val | Ser | Pro | Phe | Asp | Asn | Gly | Arg | Val | Phe |      |
|     |     |     | 100 |     |     |     |     | 105 |     |     |     |     | 110 |     |     |      |
| tat | acc | aat | tcc | ggc | tcc | gag | gcg | aac | gac | acc | atg | gtc | aag | atg | ctg | 384  |
| Tyr | Thr | Asn | Ser | Gly | Ser | Glu | Ala | Asn | Asp | Thr | Met | Val | Lys | Met | Leu |      |
|     |     |     | 115 |     |     |     |     | 120 |     |     |     |     | 125 |     |     |      |
| tgg | ttc | ctg | cat | gcc | gcc | gag | ggc | aag | ccg | caa | aag | cgc | aag | atc | ctg | 432  |
| Trp | Phe | Leu | His | Ala | Ala | Glu | Gly | Lys | Pro | Gln | Lys | Arg | Lys | Ile | Leu |      |
|     |     |     | 130 |     |     |     |     | 135 |     |     |     |     | 140 |     |     |      |
| acg | cgc | tgg | aac | gcc | tat | cac | ggc | gtg | acc | gcg | gtt | tcg | gcc | tcg | atg | 480  |
| Thr | Arg | Trp | Asn | Ala | Tyr | His | Gly | Val | Thr | Ala | Val | Ser | Ala | Ser | Met |      |
| 145 |     |     |     |     | 150 |     |     |     |     | 155 |     |     |     |     | 160 |      |
| acc | ggc | aag | ccc | tac | aac | tcg | gtc | ttc | ggc | ctg | ccg | ctg | ccc | ggc | ttc | 528  |
| Thr | Gly | Lys | Pro | Tyr | Asn | Ser | Val | Phe | Gly | Leu | Pro | Leu | Pro | Gly | Phe |      |
|     |     |     |     | 165 |     |     |     |     | 170 |     |     |     |     | 175 |     |      |
| atc | cac | ctg | acc | tgc | ccg | cat | tac | tgg | cgc | tat | ggc | gag | gaa | ggc | gag | 576  |
| Ile | His | Leu | Thr | Cys | Pro | His | Tyr | Trp | Arg | Tyr | Gly | Glu | Glu | Gly | Glu |      |
|     |     |     | 180 |     |     |     |     | 185 |     |     |     |     | 190 |     |     |      |
| acc | gag | gcg | caa | ttc | gtc | gcc | cgc | ctg | gca | cgc | gag | ctt | gag | gat | acc | 624  |
| Thr | Glu | Ala | Gln | Phe | Val | Ala | Arg | Leu | Ala | Arg | Glu | Leu | Glu | Asp | Thr |      |
|     |     |     | 195 |     |     |     |     | 200 |     |     |     |     | 205 |     |     |      |
| atc | acc | cgc | gag | ggc | gcc | gac | acc | atc | gcc | ggc | ttc | ttc | gcc | gag | ccg | 672  |
| Ile | Thr | Arg | Glu | Gly | Ala | Asp | Thr | Ile | Ala | Gly | Phe | Phe | Ala | Glu | Pro |      |
|     |     |     | 210 |     |     |     |     | 215 |     |     |     |     | 220 |     |     |      |
| gtg | atg | ggc | gcg | ggg | ggg | gtg | atc | ccg | ccg | gcg | aag | ggt | tat | ttc | cag | 720  |
| Val | Met | Gly | Ala | Gly | Gly | Val | Ile | Pro | Pro | Ala | Lys | Gly | Tyr | Phe | Gln |      |
| 225 |     |     |     |     | 230 |     |     |     |     | 235 |     |     |     |     | 240 |      |
| gcc | atc | ctg | ccg | atc | ttg | cgc | aag | tat | gac | atc | ccg | atg | atc | tcg | gac | 768  |
| Ala | Ile | Leu | Pro | Ile | Leu | Arg | Lys | Tyr | Asp | Ile | Pro | Met | Ile | Ser | Asp |      |
|     |     |     |     | 245 |     |     |     |     | 250 |     |     |     |     | 255 |     |      |
| gag | gtg | atc | tgc | ggc | ttc | ggg | cgc | acc | ggc | aac | acc | tgg | ggc | tgc | ctg | 816  |
| Glu | Val | Ile | Cys | Gly | Phe | Gly | Arg | Thr | Gly | Asn | Thr | Trp | Gly | Cys | Leu |      |
|     |     |     | 260 |     |     |     |     | 265 |     |     |     |     | 270 |     |     |      |
| acc | tac | gac | ttc | atg | ccc | gat | gcg | atc | atc | tcg | tcc | aag | aac | ctg | act | 864  |
| Thr | Tyr | Asp | Phe | Met | Pro | Asp | Ala | Ile | Ile | Ser | Ser | Lys | Asn | Leu | Thr |      |
|     |     |     | 275 |     |     |     |     | 280 |     |     |     |     | 285 |     |     |      |
| gcg | ggc | ttc | ttc | ccg | atg | ggc | gcc | gtc | atc | ctc | ggg | ccc | gac | ctc | gcc | 912  |
| Ala | Gly | Phe | Phe | Pro | Met | Gly | Ala | Val | Ile | Leu | Gly | Pro | Asp | Leu | Ala |      |
|     | 290 |     |     |     |     | 295 |     |     |     |     | 300 |     |     |     |     |      |
| aag | cgg | gtc | gag | gcc | gcg | gtc | gag | gcg | atc | gag | gag | ttc | ccg | cac | ggc | 960  |
| Lys | Arg | Val | Glu | Ala | Ala | Val | Glu | Ala | Ile | Glu | Glu | Phe | Pro | His | Gly |      |
| 305 |     |     |     |     | 310 |     |     |     |     | 315 |     |     |     |     | 320 |      |
| ttc | acc | gcc | tcg | ggc | cat | ccg | gtc | ggc | tgc | gcc | atc | gcg | ctg | aag | gcc | 1008 |
| Phe | Thr | Ala | Ser | Gly | His | Pro | Val | Gly | Cys | Ala | Ile | Ala | Leu | Lys | Ala |      |
|     |     |     |     | 325 |     |     |     |     | 330 |     |     |     |     | 335 |     |      |
| atc | gac | gtg | gtg | atg | aac | gag | ggg | ctg | gcc | gag | aat | gtc | cgc | cgc | ctc | 1056 |
| Ile | Asp | Val | Val | Met | Asn | Glu | Gly | Leu | Ala | Glu | Asn | Val | Arg | Arg | Leu |      |
|     |     |     | 340 |     |     |     |     | 345 |     |     |     |     | 350 |     |     |      |
| gca | ccc | cgc | ttc | gag | gcg | ggg | ctg | aag | cgc | atc | gcc | gac | cgc | ccg | aac | 1104 |
| Ala | Pro | Arg | Phe | Glu | Ala | Gly | Leu | Lys | Arg | Ile | Ala | Asp | Arg | Pro | Asn |      |
|     | 355 |     |     |     |     | 360 |     |     |     |     | 365 |     |     |     |     |      |
| atc | ggc | gaa | tac | cgc | ggc | atc | ggc | ttc | atg | tgg | gcg | ctg | gag | gcg | gtc | 1152 |
| Ile | Gly | Glu | Tyr | Arg | Gly | Ile | Gly | Phe | Met | Trp | Ala | Leu | Glu | Ala | Val |      |
|     | 370 |     |     |     |     | 375 |     |     |     |     | 380 |     |     |     |     |      |
| aag | gac | aag | ccg | acc | aag | acc | ccc | ttc | gac | gcc | aat | ctt | tcg | gtc | agc | 1200 |
| Lys | Asp | Lys | Pro | Thr | Lys | Thr | Pro | Phe | Asp | Ala | Asn | Leu | Ser | Val | Ser |      |
| 385 |     |     |     |     | 390 |     |     |     |     | 395 |     |     |     |     | 400 |      |
| gag | cgc | atc | gcc | aat | acc | tgc | acc | gat | ctg | ggg | ctg | atc | tgc | cgg | ccg | 1248 |

```
Glu Arg Ile Ala Asn Thr Cys Thr Asp Leu Gly Leu Ile Cys Arg Pro
                405                 410                 415
ctg ggc cag tcc atc gtg ctg tgc ccg ccc ttc atc ctg acc gag gcg    1296
Leu Gly Gln Ser Ile Val Leu Cys Pro Pro Phe Ile Leu Thr Glu Ala
        420                 425                 430
cag atg gac gag atg ttc gaa aag ctg gaa aag gcg ctc gac aag gtc    1344
Gln Met Asp Glu Met Phe Glu Lys Leu Glu Lys Ala Leu Asp Lys Val
    435                 440                 445
ttt gcc gag gtg gcc tga                                            1362
Phe Ala Glu Val Ala
    450

<210> SEQ ID NO 15
<211> LENGTH: 453
<212> TYPE: PRT
<213> ORGANISM: Paracoccus denitrificans

<400> SEQUENCE: 15

Met Asn Gln Pro Gln Ser Trp Glu Ala Arg Ala Glu Thr Tyr Ser Leu
1               5                   10                  15

Tyr Gly Phe Thr Asp Met Pro Ser Val His Gln Arg Gly Thr Val Val
            20                  25                  30

Val Thr His Gly Glu Gly Pro Tyr Ile Val Asp Val His Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Glu Ala Ala Lys Ala Gln Tyr Asp Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Asn Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Ile His Leu Thr Cys Pro His Tyr Trp Arg Tyr Gly Glu Glu Gly Glu
            180                 185                 190

Thr Glu Ala Gln Phe Val Ala Arg Leu Ala Arg Glu Leu Glu Asp Thr
        195                 200                 205

Ile Thr Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Met Ile Ser Asp
                245                 250                 255

Glu Val Ile Cys Gly Phe Gly Arg Thr Gly Asn Thr Trp Gly Cys Leu
            260                 265                 270

Thr Tyr Asp Phe Met Pro Asp Ala Ile Ile Ser Ser Lys Asn Leu Thr
        275                 280                 285

Ala Gly Phe Phe Pro Met Gly Ala Val Ile Leu Gly Pro Asp Leu Ala
    290                 295                 300
```

```
Lys Arg Val Glu Ala Ala Val Glu Ala Ile Glu Glu Phe Pro His Gly
305                 310                 315                 320

Phe Thr Ala Ser Gly His Pro Val Gly Cys Ala Ile Ala Leu Lys Ala
            325                 330                 335

Ile Asp Val Val Met Asn Glu Gly Leu Ala Glu Asn Val Arg Arg Leu
        340                 345                 350

Ala Pro Arg Phe Glu Ala Gly Leu Lys Arg Ile Ala Asp Arg Pro Asn
    355                 360                 365

Ile Gly Glu Tyr Arg Gly Ile Gly Phe Met Trp Ala Leu Glu Ala Val
370                 375                 380

Lys Asp Lys Pro Thr Lys Thr Pro Phe Asp Ala Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Ile Val Leu Cys Pro Pro Phe Ile Leu Thr Glu Ala
            420                 425                 430

Gln Met Asp Glu Met Phe Glu Lys Leu Glu Lys Ala Leu Asp Lys Val
        435                 440                 445

Phe Ala Glu Val Ala
    450

<210> SEQ ID NO 16
<211> LENGTH: 1350
<212> TYPE: DNA
<213> ORGANISM: Bacillus weihenstephanensis
<220> FEATURE:
<221> NAME/KEY: CDS
<222> LOCATION: (1)..(1350)
<223> OTHER INFORMATION: aminotransferase zp01186960

<400> SEQUENCE: 16 atg caa gcg acg gag caa aca caa agt ttg aaa aaa aca gat gaa aag      48
Met Gln Ala Thr Glu Gln Thr Gln Ser Leu Lys Lys Thr Asp Glu Lys
1               5                   10                  15 tac ctt tgg cat gcg atg aga gga gca gcc cct agt cca acg aat tta      96
Tyr Leu Trp His Ala Met Arg Gly Ala Ala Pro Ser Pro Thr Asn Leu
            20                  25                  30 att atc aca aaa gca gaa ggg gca tgg gtg acg gat att gat gga aac     144
Ile Ile Thr Lys Ala Glu Gly Ala Trp Val Thr Asp Ile Asp Gly Asn
        35                  40                  45 cgt tat tta gac ggt atg tcc ggt ctt tgg tgc gtg aat gtt ggg tat     192
Arg Tyr Leu Asp Gly Met Ser Gly Leu Trp Cys Val Asn Val Gly Tyr
    50                  55                  60 ggt cga aaa gaa ctt gca aga gcg gcg ttt gaa cag ctt gaa gaa atg     240
Gly Arg Lys Glu Leu Ala Arg Ala Ala Phe Glu Gln Leu Glu Glu Met
65                  70                  75                  80 ccg tat ttc cct ctg act caa agt cat gtt cct gct att aaa tta gca     288
Pro Tyr Phe Pro Leu Thr Gln Ser His Val Pro Ala Ile Lys Leu Ala
            85                  90                  95 gaa aaa ttg aat gaa tgg ctt gat gat gaa tac gtc att ttc ttt tct     336
Glu Lys Leu Asn Glu Trp Leu Asp Asp Glu Tyr Val Ile Phe Phe Ser
        100                 105                 110 aac agt gga tcg gaa gcg aat gaa aca gca ttt aaa att gct cgt caa     384
Asn Ser Gly Ser Glu Ala Asn Glu Thr Ala Phe Lys Ile Ala Arg Gln
    115                 120                 125 tat cat caa caa aaa ggt gat cat gga cgc tat aag ttt att tcc cgc     432
Tyr His Gln Gln Lys Gly Asp His Gly Arg Tyr Lys Phe Ile Ser Arg
130                 135                 140
```

-continued

| | | |
|---|---|---|
| tac cgc gct tat cac ggt aac tca atg gga gct ctt gca gca aca ggt<br>Tyr Arg Ala Tyr His Gly Asn Ser Met Gly Ala Leu Ala Ala Thr Gly<br>145                         150                 155               160 | | 480 |
| caa gca cag cga aag tat aaa tat gaa cca ctc ggg caa gga ttc ctg<br>Gln Ala Gln Arg Lys Tyr Lys Tyr Glu Pro Leu Gly Gln Gly Phe Leu<br>                165                 170                 175 | | 528 |
| cat gta gca ccg cct gat acg tat cga aat cca gag gat gtt cat aca<br>His Val Ala Pro Pro Asp Thr Tyr Arg Asn Pro Glu Asp Val His Thr<br>              180                    185               190 | | 576 |
| ctg gca agt gct gag gaa atc gat cgt gtc atg aca tgg gag tta agc<br>Leu Ala Ser Ala Glu Glu Ile Asp Arg Val Met Thr Trp Glu Leu Ser<br>        195                200               205 | | 624 |
| caa aca gta gcc ggt gtg att atg gag cca atc att act ggg ggc gga<br>Gln Thr Val Ala Gly Val Ile Met Glu Pro Ile Ile Thr Gly Gly Gly<br>210                         215                 220 | | 672 |
| att tta atg cct cct gat gga tat atg gga aaa gta aaa gaa att tgc<br>Ile Leu Met Pro Pro Asp Gly Tyr Met Gly Lys Val Lys Glu Ile Cys<br>225                         230               235               240 | | 720 |
| gag aag cac ggt gcg ttg ctc att tgt gat gaa gtt ata tgt gga ttt<br>Glu Lys His Gly Ala Leu Leu Ile Cys Asp Glu Val Ile Cys Gly Phe<br>                       245                 250               255 | | 768 |
| ggc cgg aca ggg aag cca ttt gga ttt atg aat tat ggc gtc aaa cca<br>Gly Arg Thr Gly Lys Pro Phe Gly Phe Met Asn Tyr Gly Val Lys Pro<br>            260                    265               270 | | 816 |
| gat atc att aca atg gca aaa ggt att aca agt gcg tat ctt cct ttg<br>Asp Ile Ile Thr Met Ala Lys Gly Ile Thr Ser Ala Tyr Leu Pro Leu<br>              275                   280               285 | | 864 |
| tca gca aca gca gtt aga cga gag gtt tat gag gca ttc gta ggt agt<br>Ser Ala Thr Ala Val Arg Arg Glu Val Tyr Glu Ala Phe Val Gly Ser<br>290                         295               300 | | 912 |
| gat gat tat gat cgc ttc cgc cat gta aat acg ttc gga ggg aat cct<br>Asp Asp Tyr Asp Arg Phe Arg His Val Asn Thr Phe Gly Gly Asn Pro<br>305                         310               315               320 | | 960 |
| gct gct tgc gct tta gct ttg aag aat tta gaa att atg gag aat gag<br>Ala Ala Cys Ala Leu Ala Leu Lys Asn Leu Glu Ile Met Glu Asn Glu<br>                       325                 330               335 | | 1008 |
| aaa ctc att gaa cgt tcc aaa gaa ttg ggt gaa cga ctg tta tat gag<br>Lys Leu Ile Glu Arg Ser Lys Glu Leu Gly Glu Arg Leu Leu Tyr Glu<br>                340                 345               350 | | 1056 |
| cta gag gat gta aaa gag cat cca aac gta ggg gat gtt cgc gga aag<br>Leu Glu Asp Val Lys Glu His Pro Asn Val Gly Asp Val Arg Gly Lys<br>             355                   360               365 | | 1104 |
| ggc ctt ctt tta ggc att gaa cta gtg gaa gat aag caa aca aaa gaa<br>Gly Leu Leu Leu Gly Ile Glu Leu Val Glu Asp Lys Gln Thr Lys Glu<br>     370                   375               380 | | 1152 |
| ccg gct tcc att gaa aag atg aac aaa gtc atc aat gct tgt aaa gaa<br>Pro Ala Ser Ile Glu Lys Met Asn Lys Val Ile Asn Ala Cys Lys Glu<br>385                         390               395               400 | | 1200 |
| aaa ggt cta att att ggt aaa aat ggt gac act gtc gca ggt tac aat<br>Lys Gly Leu Ile Ile Gly Lys Asn Gly Asp Thr Val Ala Gly Tyr Asn<br>                       405                 410               415 | | 1248 |
| aat att ttg cag ctt gca cct cca tta agc atc aca gag gaa gac ttt<br>Asn Ile Leu Gln Leu Ala Pro Pro Leu Ser Ile Thr Glu Glu Asp Phe<br>                  420                 425               430 | | 1296 |
| act ttt atc gtt aaa aca atg aaa gaa tgt tta tcc cgc att aac ggg<br>Thr Phe Ile Val Lys Thr Met Lys Glu Cys Leu Ser Arg Ile Asn Gly<br>              435                   440               445 | | 1344 |
| cag taa<br>Gln | | 1350 |

<210> SEQ ID NO 17
<211> LENGTH: 449
<212> TYPE: PRT
<213> ORGANISM: Bacillus weihenstephanensis

<400> SEQUENCE: 17

```
Met Gln Ala Thr Glu Gln Thr Gln Ser Leu Lys Lys Thr Asp Glu Lys
 1               5                  10                  15

Tyr Leu Trp His Ala Met Arg Gly Ala Ala Pro Ser Pro Thr Asn Leu
            20                  25                  30

Ile Ile Thr Lys Ala Glu Gly Ala Trp Val Thr Asp Ile Asp Gly Asn
        35                  40                  45

Arg Tyr Leu Asp Gly Met Ser Gly Leu Trp Cys Val Asn Val Gly Tyr
50                  55                  60

Gly Arg Lys Glu Leu Ala Arg Ala Ala Phe Glu Gln Leu Glu Glu Met
65                  70                  75                  80

Pro Tyr Phe Pro Leu Thr Gln Ser His Val Pro Ala Ile Lys Leu Ala
                85                  90                  95

Glu Lys Leu Asn Glu Trp Leu Asp Asp Glu Tyr Val Ile Phe Phe Ser
            100                 105                 110

Asn Ser Gly Ser Glu Ala Asn Glu Thr Ala Phe Lys Ile Ala Arg Gln
        115                 120                 125

Tyr His Gln Gln Lys Gly Asp His Gly Arg Tyr Lys Phe Ile Ser Arg
130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
                165                 170                 175

His Val Ala Pro Pro Asp Thr Tyr Arg Asn Pro Glu Asp Val His Thr
            180                 185                 190

Leu Ala Ser Ala Glu Glu Ile Asp Arg Val Met Thr Trp Glu Leu Ser
        195                 200                 205

Gln Thr Val Ala Gly Val Ile Met Glu Pro Ile Ile Thr Gly Gly Gly
210                 215                 220

Ile Leu Met Pro Pro Asp Gly Tyr Met Gly Lys Val Lys Glu Ile Cys
225                 230                 235                 240

Glu Lys His Gly Ala Leu Leu Ile Cys Asp Glu Val Ile Cys Gly Phe
                245                 250                 255

Gly Arg Thr Gly Lys Pro Phe Gly Phe Met Asn Tyr Gly Val Lys Pro
            260                 265                 270

Asp Ile Ile Thr Met Ala Lys Gly Ile Thr Ser Ala Tyr Leu Pro Leu
        275                 280                 285

Ser Ala Thr Ala Val Arg Arg Glu Val Tyr Glu Ala Phe Val Gly Ser
290                 295                 300

Asp Asp Tyr Asp Arg Phe Arg His Val Asn Thr Phe Gly Gly Asn Pro
305                 310                 315                 320

Ala Ala Cys Ala Leu Ala Leu Lys Asn Leu Glu Ile Met Glu Asn Glu
                325                 330                 335

Lys Leu Ile Glu Arg Ser Lys Gly Leu Gly Arg Leu Leu Tyr Glu
            340                 345                 350

Leu Glu Asp Val Lys Glu His Pro Asn Val Gly Asp Val Arg Gly Lys
        355                 360                 365

Gly Leu Leu Leu Gly Ile Glu Leu Val Glu Asp Lys Gln Thr Lys Glu
370                 375                 380
```

```
Pro Ala Ser Ile Glu Lys Met Asn Lys Val Ile Asn Ala Cys Lys Glu
385                 390                 395                 400

Lys Gly Leu Ile Ile Gly Lys Asn Gly Asp Thr Val Ala Gly Tyr Asn
            405                 410                 415

Asn Ile Leu Gln Leu Ala Pro Pro Leu Ser Ile Thr Glu Glu Asp Phe
        420                 425                 430

Thr Phe Ile Val Lys Thr Met Lys Glu Cys Leu Ser Arg Ile Asn Gly
    435                 440                 445

Gln

<210> SEQ ID NO 18
<211> LENGTH: 1350
<212> TYPE: DNA
<213> ORGANISM: artificial
<220> FEATURE:
<223> OTHER INFORMATION: coodon-optimized sequence of aminotransferase
      zp01186960

<400> SEQUENCE: 18
```

| | | | | | |
|---|---|---|---|---|---|
| atgcaggcta | ccgaacaaac | ccaatctctg | aaaaagactg | acgaaaaata | tctgtggcac | 60 |
| gcgatgcgcg | gtgcagctcc | gtctccgacc | aacctgatta | ttaccaaagc | tgaaggcgcg | 120 |
| tgggtgaccg | acattgacgg | taaccgttat | ctggatggca | tgagcggcct | gtggtgtgtt | 180 |
| aatgtcggtt | atggccgtaa | ggagctggcc | gcgcgcggca | ttgacaact | ggaagaaatg | 240 |
| ccgtacttcc | cgctgactca | aagccatgtg | ccggctatca | aactggcgga | aaaactgaac | 300 |
| gaatggctgg | acgacgaata | cgtgattttc | ttctctaatt | ctggctccga | agcaaacgaa | 360 |
| accgcattca | aaatcgcccg | tcaatatcac | agcagaaaag | gtgaccacgg | ccgctataaa | 420 |
| ttcatcagcc | gttatcgtgc | ataccatggt | aattctatgg | gtgcgctggc | tgctaccggt | 480 |
| caggctcagc | gcaaatacaa | gtacgaaccg | ctgggtcagg | gttttctgca | cgttgcacca | 540 |
| ccggatacct | accgtaaccc | ggaagacgtc | cacaccctgg | cttctgccga | gaaaatcgat | 600 |
| cgtgttatga | cctgggagct | gtcccagact | gttgcgggtg | ttatcatgga | acctattatt | 660 |
| accggtggtg | gcattctgat | gccgccggac | ggttatatgg | gtaaagtcaa | ggaaatctgc | 720 |
| gaaaaacacg | gcgcgctgct | gatctgcgat | gaagttatct | gtggcttcgg | tcgcaccggc | 780 |
| aaaccatttg | gcttcatgaa | ttatggcgta | aaacctgaca | ttattaccat | ggctaaaggc | 840 |
| attacttccg | cttatctgcc | gctgagcgcg | accgcagttc | gccgcgaagt | ttatgaagcg | 900 |
| tttgttggtt | ctgatgatta | cgaccgtttc | cgtcatgtaa | acacgtttgg | cggtaaccca | 960 |
| gcggcatgtg | cgctggcgct | gaaaaacctg | gaaatcatgg | aaaacgaaaa | gctgatcgaa | 1020 |
| cgtagcaaag | aactgggtga | acgtctgctg | tacgaactgg | aagatgtcaa | agaacacccg | 1080 |
| aacgtgggcg | atgttcgcgg | taaaggcctg | ctgctgggta | ttgaactggt | tgaagacaaa | 1140 |
| cagaccaagg | aaccggcttc | cattgaaaag | atgaacaaag | tgattaacgc | gtgcaaagag | 1200 |
| aaaggcctga | tcattggtaa | gaacggtgat | accgtggcag | gttataacaa | cattctgcag | 1260 |
| ctggcgccgc | ctctgagcat | cactgaagaa | gatttcacct | tcatcgtcaa | aactatgaag | 1320 |
| gagtgcctga | gccgcatcaa | tggtcagtaa | | | | 1350 |

```
<210> SEQ ID NO 19
<211> LENGTH: 300
<212> TYPE: PRT
<213> ORGANISM: Bacillus amyloliquefaciens
```

```
<220> FEATURE:
<221> NAME/KEY: mat_peptide
<222> LOCATION: (1)..(300)
<223> OTHER INFORMATION: Protease B

<400> SEQUENCE: 19
```

| | | | | | | | | | | | | | | |
|---|---|---|---|---|---|---|---|---|---|---|---|---|---|---|
| Ala | Ala | Thr | Thr | Gly | Thr | Gly | Thr | Thr | Leu | Lys | Gly | Lys | Thr | Val | Ser |
| 1 | | | | 5 | | | | | 10 | | | | | 15 | |
| Leu | Asn | Ile | Ser | Ser | Glu | Ser | Gly | Lys | Tyr | Val | Leu | Arg | Asp | Leu | Ser |
| | | | 20 | | | | | 25 | | | | | 30 | | |
| Lys | Pro | Thr | Gly | Thr | Gln | Ile | Ile | Thr | Tyr | Asp | Leu | Gln | Asn | Arg | Glu |
| | | 35 | | | | | 40 | | | | | 45 | | | |
| Tyr | Asn | Leu | Pro | Gly | Thr | Leu | Val | Ser | Ser | Thr | Thr | Asn | Gln | Phe | Thr |
| 50 | | | | | 55 | | | | | 60 | | | | | |
| Thr | Ser | Ser | Gln | Arg | Ala | Ala | Val | Asp | Ala | His | Tyr | Asn | Leu | Gly | Lys |
| 65 | | | | | 70 | | | | | 75 | | | | | 80 |
| Val | Tyr | Asp | Tyr | Phe | Tyr | Gln | Lys | Phe | Asn | Arg | Asn | Ser | Tyr | Asp | Asn |
| | | | | 85 | | | | | 90 | | | | | 95 | |
| Lys | Gly | Gly | Lys | Ile | Val | Ser | Ser | Val | His | Tyr | Gly | Ser | Arg | Tyr | Asn |
| | | | 100 | | | | | 105 | | | | | 110 | | |
| Asn | Ala | Ala | Trp | Ile | Gly | Asp | Gln | Met | Ile | Tyr | Gly | Asp | Gly | Asp | Gly |
| | | 115 | | | | | 120 | | | | | 125 | | | |
| Ser | Phe | Phe | Ser | Pro | Leu | Ser | Gly | Ser | Met | Asp | Val | Thr | Ala | His | Glu |
| 130 | | | | | 135 | | | | | 140 | | | | | |
| Met | Thr | His | Gly | Val | Thr | Gln | Glu | Thr | Ala | Asn | Leu | Asn | Tyr | Glu | Asn |
| 145 | | | | | 150 | | | | | 155 | | | | | 160 |
| Gln | Pro | Gly | Ala | Leu | Asn | Glu | Ser | Phe | Ser | Asp | Val | Phe | Gly | Tyr | Phe |
| | | | | 165 | | | | | 170 | | | | | 175 | |
| Asn | Asp | Thr | Glu | Asp | Trp | Asp | Ile | Gly | Glu | Asp | Ile | Thr | Val | Ser | Gln |
| | | | 180 | | | | | 185 | | | | | 190 | | |
| Pro | Ala | Leu | Arg | Ser | Leu | Ser | Asn | Pro | Thr | Lys | Tyr | Gly | Gln | Pro | Asp |
| | | 195 | | | | | 200 | | | | | 205 | | | |
| Asn | Phe | Lys | Asn | Tyr | Lys | Asn | Leu | Pro | Asn | Thr | Asp | Ala | Gly | Asp | Tyr |
| 210 | | | | | 215 | | | | | 220 | | | | | |
| Gly | Gly | Val | His | Thr | Asn | Ser | Gly | Ile | Pro | Asn | Lys | Ala | Ala | Tyr | Asn |
| 225 | | | | | 230 | | | | | 235 | | | | | 240 |
| Thr | Ile | Thr | Lys | Ile | Gly | Val | Asn | Lys | Ala | Glu | Gln | Ile | Tyr | Tyr | Arg |
| | | | | 245 | | | | | 250 | | | | | 255 | |
| Ala | Leu | Thr | Val | Tyr | Leu | Thr | Pro | Ser | Ser | Thr | Phe | Lys | Asp | Ala | Lys |
| | | | 260 | | | | | 265 | | | | | 270 | | |
| Ala | Ala | Leu | Ile | Gln | Ser | Ala | Arg | Asp | Leu | Tyr | Gly | Ser | Gln | Asp | Ala |
| | | 275 | | | | | 280 | | | | | 285 | | | |
| Ala | Ser | Val | Glu | Ala | Ala | Trp | Asn | Ala | Val | Gly | Leu | | | | |
| | 290 | | | | | 295 | | | | | 300 | | | | |

```
<210> SEQ ID NO 20
<211> LENGTH: 274
<212> TYPE: PRT
<213> ORGANISM: Bacillus licheniformis
<220> FEATURE:
<221> NAME/KEY: mat_peptide
<222> LOCATION: (1)..(274)
<223> OTHER INFORMATION: Delvolase
```

<400> SEQUENCE: 20

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Thr Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Ser Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 21
<211> LENGTH: 1647
<212> TYPE: DNA
<213> ORGANISM: Sus scrofa
<220> FEATURE:
<221> NAME/KEY: CDS
<222> LOCATION: (1)..(1647)
<223> OTHER INFORMATION: alternative pig liver esterase

<400> SEQUENCE: 21

```
ggg cag cca gcc tcg ccg cct gtt gtg gac act gcc cag ggc cga gtc      48
Gly Gln Pro Ala Ser Pro Pro Val Val Asp Thr Ala Gln Gly Arg Val
1               5                   10                  15 ctg ggg aag tac gtc agc tta gaa ggc ctg gca cag ccg gtg gcc gtc      96
Leu Gly Lys Tyr Val Ser Leu Glu Gly Leu Ala Gln Pro Val Ala Val
            20                  25                  30 ttc ctg gga gtc cct ttt gcc aag ccc cct ctc gga tcc ttg agg ttt     144
Phe Leu Gly Val Pro Phe Ala Lys Pro Pro Leu Gly Ser Leu Arg Phe
        35                  40                  45
```

```
gct ccg ccg cag cct gca gaa cca tgg agc ttc gtg aag aac acc acc    192
Ala Pro Pro Gln Pro Ala Glu Pro Trp Ser Phe Val Lys Asn Thr Thr
 50              55                  60 tcc tac cct ccc atg tgc tgc caa gag cca att ggg gga cag atg ctc    240
Ser Tyr Pro Pro Met Cys Cys Gln Glu Pro Ile Gly Gly Gln Met Leu
 65              70                  75                      80 tca gat cta ttt acc aac aga aag gag agg ctc att ccg gag ttt tct    288
Ser Asp Leu Phe Thr Asn Arg Lys Glu Arg Leu Ile Pro Glu Phe Ser
                 85                  90                  95 gaa gac tgt ctc tac cta aat att tac acc cct gct gac ctg aca aag    336
Glu Asp Cys Leu Tyr Leu Asn Ile Tyr Thr Pro Ala Asp Leu Thr Lys
            100                 105                 110 agg ggc aga ctg ccg gtg atg gtg tgg atc cac gga gga ggt ctg gtg    384
Arg Gly Arg Leu Pro Val Met Val Trp Ile His Gly Gly Gly Leu Val
        115                 120                 125 gtg ggc ggg gct tcc acc tat gat gga ctg gcc ctc gct gcg cat gaa    432
Val Gly Gly Ala Ser Thr Tyr Asp Gly Leu Ala Leu Ala Ala His Glu
130                 135                 140 aac gtg gtg gtg gtg gcc atc cag tac cgc ctg ggc atc tgg gga ttc    480
Asn Val Val Val Val Ala Ile Gln Tyr Arg Leu Gly Ile Trp Gly Phe
145                 150                 155                 160 ttc agc aca ggg gac gaa cac agc cgg ggc aac tgg ggt cac ttg gac    528
Phe Ser Thr Gly Asp Glu His Ser Arg Gly Asn Trp Gly His Leu Asp
                165                 170                 175 cag gtg gcc gca ctg cac tgg gtc cag gag aac atc gcc aac ttt gga    576
Gln Val Ala Ala Leu His Trp Val Gln Glu Asn Ile Ala Asn Phe Gly
            180                 185                 190 ggc gac cca ggc tct gtg acc atc ttt gga gag tca gca gga ggg gaa    624
Gly Asp Pro Gly Ser Val Thr Ile Phe Gly Glu Ser Ala Gly Gly Glu
        195                 200                 205 agt gtc tct gtt ctg gtg ttg tct ccc ttg gcc aag aac ctc ttc cac    672
Ser Val Ser Val Leu Val Leu Ser Pro Leu Ala Lys Asn Leu Phe His
210                 215                 220 cgg gcc atc tct gag agt ggc gtg gcc ttc act gct ggc ctg gtc agg    720
Arg Ala Ile Ser Glu Ser Gly Val Ala Phe Thr Ala Gly Leu Val Arg
225                 230                 235                 240 aag gac atg aag gct gca gct aag caa att gct gtc ctt gct ggg tgt    768
Lys Asp Met Lys Ala Ala Ala Lys Gln Ile Ala Val Leu Ala Gly Cys
                245                 250                 255 aaa acc acc acc tcg gct gtc ttt gtt cac tgc ctg cgc cag aag tcg    816
Lys Thr Thr Thr Ser Ala Val Phe Val His Cys Leu Arg Gln Lys Ser
            260                 265                 270 gag gac gag ctc ttg gac tta acg ctg aag atg aaa ttt ttc gct ctt    864
Glu Asp Glu Leu Leu Asp Leu Thr Leu Lys Met Lys Phe Phe Ala Leu
        275                 280                 285 gat ttg cat gga gac ccc aga gag agc cat ccc ttc ctg acc act gtg    912
Asp Leu His Gly Asp Pro Arg Glu Ser His Pro Phe Leu Thr Thr Val
290                 295                 300 gtg gat gga gtg ctg ctg ccc aag atg cct gaa gag att ctg gct gaa    960
Val Asp Gly Val Leu Leu Pro Lys Met Pro Glu Glu Ile Leu Ala Glu
305                 310                 315                 320 aag gat ttc aac act gtc ccc tac atc gtg gga atc aac aag caa gag   1008
Lys Asp Phe Asn Thr Val Pro Tyr Ile Val Gly Ile Asn Lys Gln Glu
                325                 330                 335 ttt ggc tgg ctt ctg cca acg atg atg ggc ttc ccc ctc tct gaa ggc   1056
Phe Gly Trp Leu Leu Pro Thr Met Met Gly Phe Pro Leu Ser Glu Gly
            340                 345                 350 aag ctg gac cag aag acg gcc acg tca ctc ctg tgg aag tcc tac ccc   1104
Lys Leu Asp Gln Lys Thr Ala Thr Ser Leu Leu Trp Lys Ser Tyr Pro
        355                 360                 365
```

| | | | | | | | | | | | | | | | | |
|---|---|---|---|---|---|---|---|---|---|---|---|---|---|---|---|---|
| atc | gct | aac | atc | cct | gag | gaa | ctg | act | cca | gtg | gcc | act | gac | aag | tat | 1152 |
| Ile | Ala | Asn | Ile | Pro | Glu | Glu | Leu | Thr | Pro | Val | Ala | Thr | Asp | Lys | Tyr | |
| | 370 | | | | 375 | | | | | 380 | | | | | | |
| ttg | ggg | ggg | aca | gac | gac | ccc | gtc | aaa | aag | aaa | gac | ctg | ttc | ctg | gac | 1200 |
| Leu | Gly | Gly | Thr | Asp | Asp | Pro | Val | Lys | Lys | Lys | Asp | Leu | Phe | Leu | Asp | |
| 385 | | | | | 390 | | | | | 395 | | | | | 400 | |
| ttg | atg | ggg | gat | gtg | gtg | ttt | ggt | gtc | cca | tct | gtg | acg | gtg | gcc | cgt | 1248 |
| Leu | Met | Gly | Asp | Val | Val | Phe | Gly | Val | Pro | Ser | Val | Thr | Val | Ala | Arg | |
| | | | | 405 | | | | | 410 | | | | | 415 | | |
| caa | cac | aga | gat | gca | gga | gcc | ccc | acc | tac | atg | tat | gag | ttt | cag | tat | 1296 |
| Gln | His | Arg | Asp | Ala | Gly | Ala | Pro | Thr | Tyr | Met | Tyr | Glu | Phe | Gln | Tyr | |
| | | | 420 | | | | | 425 | | | | | 430 | | | |
| cgc | cca | agc | ttc | tca | tcg | gac | aag | aaa | ccc | aag | acg | gtg | atc | ggg | gac | 1344 |
| Arg | Pro | Ser | Phe | Ser | Ser | Asp | Lys | Lys | Pro | Lys | Thr | Val | Ile | Gly | Asp | |
| | | 435 | | | | | 440 | | | | | 445 | | | | |
| cac | ggg | gat | gag | atc | ttc | tcc | gtc | ttt | ggt | ttt | cca | ctg | tta | aaa | ggc | 1392 |
| His | Gly | Asp | Glu | Ile | Phe | Ser | Val | Phe | Gly | Phe | Pro | Leu | Leu | Lys | Gly | |
| | 450 | | | | 455 | | | | | 460 | | | | | | |
| gat | gcc | cca | gaa | gag | gag | gtc | agt | ctc | agc | aag | acg | gtg | atg | aaa | ttc | 1440 |
| Asp | Ala | Pro | Glu | Glu | Glu | Val | Ser | Leu | Ser | Lys | Thr | Val | Met | Lys | Phe | |
| 465 | | | | | 470 | | | | | 475 | | | | | 480 | |
| tgg | gcc | aac | ttt | gct | cgc | agt | ggg | aac | ccc | aat | ggg | gag | ggg | ctg | ccc | 1488 |
| Trp | Ala | Asn | Phe | Ala | Arg | Ser | Gly | Asn | Pro | Asn | Gly | Glu | Gly | Leu | Pro | |
| | | | | 485 | | | | | 490 | | | | | 495 | | |
| cat | tgg | ccg | atg | tac | gac | cag | gaa | gaa | ggg | tac | ctt | cag | atc | ggc | gtc | 1536 |
| His | Trp | Pro | Met | Tyr | Asp | Gln | Glu | Glu | Gly | Tyr | Leu | Gln | Ile | Gly | Val | |
| | | | 500 | | | | | 505 | | | | | 510 | | | |
| aac | acc | cag | gca | gcc | aag | agg | ctg | aaa | ggt | gaa | gaa | gtg | gcc | ttc | tgg | 1584 |
| Asn | Thr | Gln | Ala | Ala | Lys | Arg | Leu | Lys | Gly | Glu | Glu | Val | Ala | Phe | Trp | |
| | | 515 | | | | | 520 | | | | | 525 | | | | |
| aac | gat | ctc | ctg | tcc | aag | gag | gca | gca | aag | aag | cca | ccc | aag | ata | aag | 1632 |
| Asn | Asp | Leu | Leu | Ser | Lys | Glu | Ala | Ala | Lys | Lys | Pro | Pro | Lys | Ile | Lys | |
| | 530 | | | | 535 | | | | | 540 | | | | | | |
| cat | gct | gag | ctg | tga | | | | | | | | | | | | 1647 |
| His | Ala | Glu | Leu | | | | | | | | | | | | | |
| 545 | | | | | | | | | | | | | | | | |

<210> SEQ ID NO 22
<211> LENGTH: 548
<212> TYPE: PRT
<213> ORGANISM: Sus scrofa

<400> SEQUENCE: 22

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
    50                  55                  60

Ser Tyr Pro Pro Met Cys Cys Gln Glu Pro Ile Gly Gly Gln Met Leu
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

```
Val Gly Gly Ala Ser Thr Tyr Asp Gly Leu Ala Leu Ala Ala His Glu
    130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
                180                 185                 190

Gly Asp Pro Gly Ser Val Thr Ile Phe Gly Glu Ser Ala Gly Gly Glu
            195                 200                 205

Ser Val Ser Val Leu Val Leu Ser Pro Leu Ala Lys Asn Leu Phe His
    210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Phe Ala Leu
            275                 280                 285

Asp Leu His Gly Asp Pro Arg Glu Ser His Pro Phe Leu Thr Thr Val
    290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
    355                 360                 365

Ile Ala Asn Ile Pro Glu Glu Leu Thr Pro Val Ala Thr Asp Lys Tyr
    370                 375                 380

Leu Gly Gly Thr Asp Asp Pro Val Lys Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
                420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Phe Pro Leu Leu Lys Gly
    450                 455                 460

Asp Ala Pro Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Gly Tyr Leu Gln Ile Gly Val
            500                 505                 510

Asn Thr Gln Ala Ala Lys Arg Leu Lys Gly Glu Glu Val Ala Phe Trp
    515                 520                 525
```

```
Asn Asp Leu Leu Ser Lys Glu Ala Ala Lys Lys Pro Pro Lys Ile Lys
    530                 535                 540

His Ala Glu Leu
545

<210> SEQ ID NO 23
<211> LENGTH: 70
<212> TYPE: DNA
<213> ORGANISM: Artificial
<220> FEATURE:
<223> OTHER INFORMATION: Forward primer for aminotransferase of
      Pseudomonas aerogenosa gi9946143

<400> SEQUENCE: 23
ggggacaagt ttgtacaaaa aagcaggcta ggaggaatta accatgaaca gccaaatcac      60
caacgccaag                                                            70

<210> SEQ ID NO 24
<211> LENGTH: 49
<212> TYPE: DNA
<213> ORGANISM: Artificial
<220> FEATURE:
<223> OTHER INFORMATION: Reverse primer for aminotransferase of
      Pseudomonas aeruginosa gi9946143

<400> SEQUENCE: 24
ggggaccact ttgtacaaga aagctgggtt caagccagga cggcggcgg                 49

<210> SEQ ID NO 25
<211> LENGTH: 66
<212> TYPE: DNA
<213> ORGANISM: Artificial
<220> FEATURE:
<223> OTHER INFORMATION: Forward primer for aminotransferase of
      Pseudomonas aeruginosa gi9951072

<400> SEQUENCE: 25
ggggacaagt ttgtacaaaa aagcaggcta ggaggaatta accatgaacg caagactgca     60
cgccac                                                                66

<210> SEQ ID NO 26
<211> LENGTH: 48
<212> TYPE: DNA
<213> ORGANISM: Artificial
<220> FEATURE:
<223> OTHER INFORMATION: Reverse primer for aminotransferase of
      Pseudomonas aeruginosa gi9951072

<400> SEQUENCE: 26
ggggaccact ttgtacaaga aagctgggtt taccggtgac cggcgcgg                  48
```